United States Patent
Hafenrichter et al.

(10) Patent No.: US 9,950,813 B2
(45) Date of Patent: Apr. 24, 2018

(54) NON-DESTRUCTIVE INSPECTION OF AIRFOIL-SHAPED BODY USING SELF-PROPELLING ARTICULATED ROBOT

(71) Applicant: The Boeing Company, Chicago, IL (US)

(72) Inventors: Joseph L. Hafenrichter, Seattle, WA (US); Gary E. Georgeson, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 105 days.

(21) Appl. No.: 15/017,535

(22) Filed: Feb. 5, 2016

(65) Prior Publication Data

US 2017/0225804 A1    Aug. 10, 2017

(51) Int. Cl.
| | |
|---|---|
| *G01D 21/00* | (2006.01) |
| *B64F 5/00* | (2017.01) |
| *G01N 29/04* | (2006.01) |
| *G01N 29/22* | (2006.01) |
| *G01N 29/265* | (2006.01) |
| *B25J 9/16* | (2006.01) |

(52) U.S. Cl.
CPC .............. *B64F 5/0045* (2013.01); *B25J 9/162* (2013.01); *G01N 29/04* (2013.01); *G01N 29/225* (2013.01); *G01N 29/265* (2013.01); *G01N 2291/106* (2013.01); *Y10S 901/44* (2013.01)

(58) Field of Classification Search
None
See application file for complete search history.

(56) References Cited

U.S. PATENT DOCUMENTS

| | | |
|---|---|---|
| 4,146,967 A | 4/1979 | Rohner et al. |
| 5,031,458 A | 7/1991 | Young et al. |
| 5,698,787 A | 12/1997 | Parzuchowski et al. |
| 6,220,099 B1 | 4/2001 | Marti et al. |
| 6,829,959 B2 | 12/2004 | Gifford et al. |
| 7,231,826 B2 | 6/2007 | Bassi et al. |
| 7,240,556 B2 | 7/2007 | Geargeson et al. |
| 7,315,609 B2 | 1/2008 | Safai et al. |
| 7,337,673 B2 | 3/2008 | Kennedy et al. |
| 7,562,593 B2 | 7/2009 | Engelbart et al. |
| 7,640,811 B2 | 1/2010 | Kennedy et al. |
| 8,347,746 B2 | 1/2013 | Hafenrichter et al. |
| 8,983,794 B1 * | 3/2015 | Motzer ................ G01L 317/06 702/150 |
| 2006/0043303 A1 | 3/2006 | Safai et al. |

(Continued)

OTHER PUBLICATIONS

MAUS Overview; http://www.boeing.com/defense-space/support/maintenance/commercial/maus.html; 4 pages.

*Primary Examiner* — Adam D Tissot
(74) *Attorney, Agent, or Firm* — Ostrager Chong Flaherty & Broitman P.C.

(57) ABSTRACT

A robotic apparatus comprising an articulated arm mounted to a chassis and having an end effector capable of inspecting the root and tip, as well as the length between the root and tip, of an airfoil-shaped body (such as a rotorblade). The robotic apparatus has means for propelling the chassis in a spanwise direction. The chassis-mounted articulated arm facilitates the scanning of sensors over the root or tip of the airfoil-shaped body without repositioning the chassis.

22 Claims, 15 Drawing Sheets

(56) References Cited

U.S. PATENT DOCUMENTS

| | | |
|---|---|---|
| 2009/0038398 A1 | 2/2009 | Lavoie et al. |
| 2014/0182479 A1* | 7/2014 | Hafenrichter ......... B64F 5/0018 105/30 |
| 2014/0188323 A1* | 7/2014 | Kouno .................... B25J 5/007 701/23 |
| 2014/0305216 A1 | 10/2014 | Hafenrichter et al. |
| 2014/0305217 A1 | 10/2014 | Hafenrichter et al. |

* cited by examiner

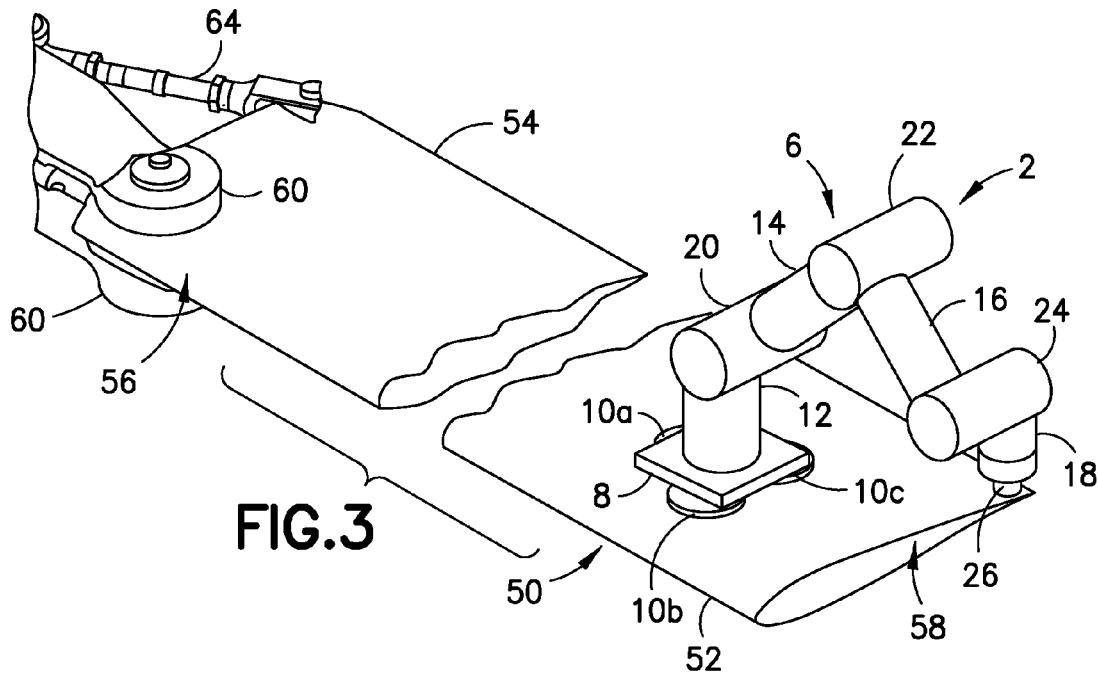
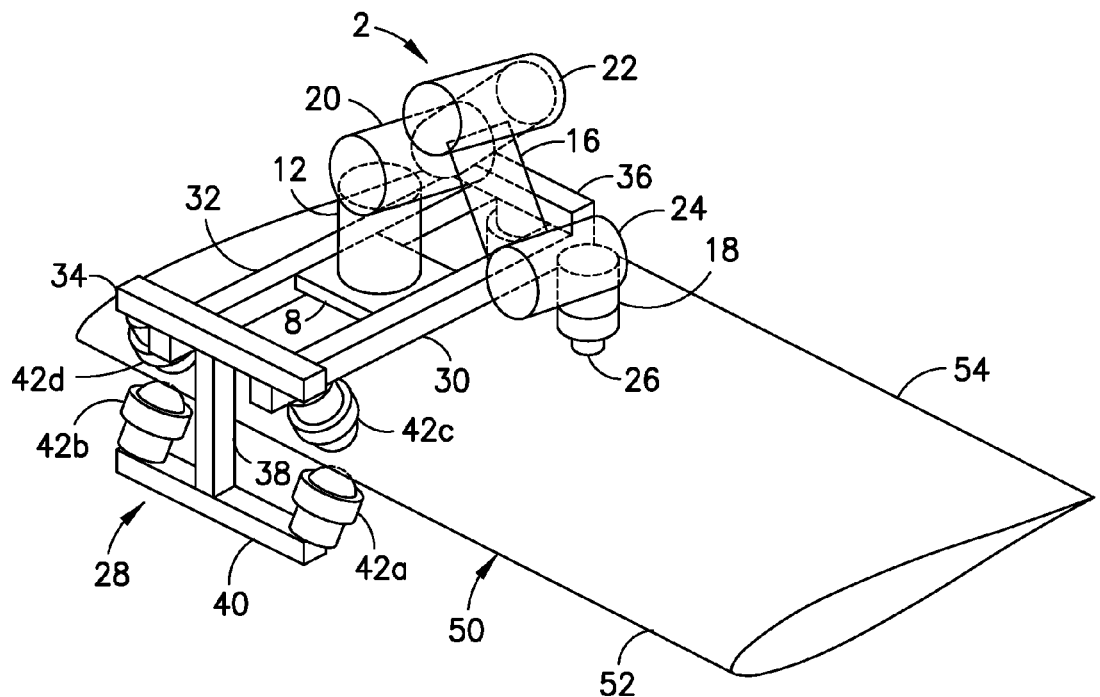

NON-DESTRUCTIVE INSPECTION OF AIRFOIL-SHAPED BODY USING SELF-PROPELLING ARTICULATED ROBOT

BACKGROUND

The present disclosure relates generally to the field of automated non-destructive inspection (NDI) of aircraft structural elements such as airfoil-shaped bodies, and more particularly to automated NDI apparatus that is coupled to and travels along an airfoil-shaped body having a relatively short chord length (such as a rotorcraft blade, an aircraft propeller blade, a winglet, a projectile fin, an aircraft horizontal stabilizer, or other types of blade component).

In order to non-destructively inspect airfoil-shaped bodies such as blade components, it is known to manually remove the blade components from the aircraft and then manually perform the inspection functions. Removal of blade components from an aircraft is cost intensive. With rotorcraft blades, for example, the time spent removing, transporting, re-attaching, balancing and trimming the blades can be significant. Some helicopters require that the blades be removed and inspected every 50-75 flight hours, resulting in a dramatically reduced mission capability of the aircraft.

In contrast, one system for non-destructive inspection of blade components during in-service use comprises an apparatus that crawls along a blade component and inspects for damage, without requiring costly removal, rebalancing, and re-installation of the blade component. The problem is that the root end of most blade components is complex, and the on-rotorcraft scanning element/method used by inspectors cannot adequately address the root end inspection without part specific scanning hardware.

Inspection of the root end of blade components (such as rotorblades) is currently done by hand, with the operator holding a probe and watching a screen for indications of damage. The drawbacks are that this is labor-intensive, relatively slow, does not provide repeatable comparable data, and is not suited for on-rotorcraft inspections, thereby requiring costly and time-consuming installation and re-balancing. A scanning bridge that travels along the span of a rotorblade can perform an automated inspection on a rotorcraft or on a bench, but only with respect to the large airfoil section of the rotorblade. The root end is currently done by hand. Also, the scanning bridge gets in the way of the inspection near the root end, so the apparatus is usually removed and turned around to do that inspection. And, the shape of many rotorblades near the tip can require hand-held NDI, because the scanning mechanism does not adequately cover the geometry of every tip.

The provision of means for inspecting the root and tips of airfoil-shaped bodies as part of the general inspection of the acreage would be advantageous.

SUMMARY

The subject matter disclosed in detail below is directed to a robotic apparatus comprising an articulated arm mounted to a chassis and having an end effector capable of inspecting the root and tip, as well as the length between the root and tip, of an airfoil-shaped body (such as a rotorblade). The robotic apparatus has means for propelling the chassis in a spanwise direction. The chassis-mounted articulated arm facilitates the scanning of sensors over the root or tip of the airfoil-shaped body without repositioning the chassis.

As used herein, the term "articulated robot" means a robot that comprises an articulated arm comprising links coupled by joints to form a "chain". The links of the articulated arm can be considered to form a kinematic chain. The proximal end of the articulated arm is coupled to a robot base by means of a twisting joint. The terminus of the kinematic chain (referred to herein as "the distal end" of the articulated arm) has an end effector coupled thereto. In the context of NDI, the end effector may be an NDI probe comprising a sensor or an array of sensors.

One aspect of the subject matter disclosed in detail below is an apparatus comprising: a chassis comprising a base and a plurality of rolling elements coupled to the base; an articulated arm having a proximal end coupled to the base of the chassis and having a distal end; a non-destructive inspection probe coupled to the distal end of the articulated arm; and at least one suction cup coupled to the base of the chassis. The apparatus may further comprise a foot (e.g., a friction foot or suction foot) coupled to the distal end of the articulated arm, wherein the foot is extendible from a retracted position to an extended position, the foot having an end extending beyond the non-destructive inspection probe when the foot is in its extended position.

Another aspect of the subject matter disclosed in detail below is a method comprising: (a) coupling a proximal end of an articulated arm to a chassis that is equipped with a plurality of suction cups and a plurality of rolling elements; (b) coupling an end effector and an extendible foot to a distal end of the articulated arm; (c) adhering the suction cups to a surface of an airfoil-shaped body; (d) operating the articulated arm so that its distal end moves adjacent to the surface of the airfoil-shaped body at a distance from the chassis; (e) extending the foot into contact with the surface of the airfoil-shaped body at the distal end of the articulated arm; (f) releasing the suction cups; (g) extending the plurality of rolling elements into contact with the surface of the airfoil-shaped body at the chassis; and (h) causing the foot to exert a force sufficient to hold the foot stationary while the chassis rolls toward the foot, wherein steps (d) and (e) are performed while the suction cups are adhered to the surface of the airfoil-shaped body, step (g) is performed while the suction cups are released, and step (h) is performed while the plurality of rolling elements are in contact with the surface of the airfoil-shaped body. The foregoing method may further comprise the following steps performed after step (h): (i) retracting the foot; (j) retracting the plurality of rolling elements; (k) re-adhering the suction cups to the surface of the airfoil-shaped body; and (l) activating the end effector to perform a non-destructive inspection task.

A further aspect is a method of non-destructive inspection comprising: (a) placing an assembly comprising an articulated arm having a proximal end coupled to a chassis so that the chassis is in contact with a first portion of a surface overlying a first portion of an airfoil-shaped body; (b) coupling an end effector to a distal end of the articulated arm; (c) adhering the chassis, using suction, to the first portion of the surface of the airfoil-shaped body; (d) operating the articulated arm so that the end effector is placed in a position for interrogating a second portion of the airfoil-shaped body; and (e) activating the end effector to interrogate the second portion of the airfoil-shaped body.

Yet another aspect of the subject matter disclosed in detail below is an automated apparatus for non-destructive inspection of an airfoil-shaped body having leading and trailing edges extending from a root to a tip, comprising: a chassis comprising a base and a plurality of rolling elements coupled to the base; a first actuatable device coupled to the base of the chassis and having a first configuration in which the first actuatable device exerts no force on a surface of an airfoil-shaped body and a second configuration in which the first actuatable device exerts a force on the surface of the airfoil-shaped body that resists movement of the base of the chassis relative to the airfoil-shaped body, wherein the first actuatable device is capable of changing its configuration from the first configuration to the second configuration in response to receipt of a first device actuation signal and changing its configuration from the second configuration to the first configuration in response to receipt of a second device actuation signal; an articulated arm comprising a proximal end coupled to the base of the chassis, a distal end, and a plurality of links coupled by motor-driven rotary joints to form a chain connecting the distal end to the proximal end, the distal end being movable relative to the proximal end in response to robot motor control signals; a non-destructive inspection probe coupled to the distal end of the articulated arm and configured to perform a non-destructive inspection task in response to a probe activation signal; a second actuatable device coupled to the distal end of the articulated arm and having a first configuration in which the second actuatable device exerts no force on the surface of the airfoil-shaped body and a second configuration in which the second actuatable device exerts a force on the surface of the airfoil-shaped body that resists movement of the distal end of the articulated arm relative to the airfoil-shaped body, wherein the second actuatable device is capable of changing its configuration from the first configuration to the second configuration in response to receipt of a third device actuation signal and changing its configuration from the second configuration to the first configuration in response to receipt of a fourth device actuation signal; and a computer system configured to perform the following operations: (a) sending the second device actuation signal to the first actuatable device; (b) after operation (a), sending robot motor control signals for operating the articulated arm so that its distal end moves to a position adjacent to the surface of the airfoil-shaped body and at a distance from the chassis; (c) sending the third device actuation signal to the second actuatable device; (d) after operation (b), sending the first device actuation signal to the first actuatable device; (e) after operation (d), sending robot motor control signals for operating the articulated arm so that its proximal end moves toward its distal end; (f) after operation (e), sending the second device actuation signal to the first actuatable device and sending the fourth device actuation signal to the second actuatable device; and (g) after operations (f), sending the probe activation signal to the non-destructive inspection probe. The automated apparatus may further comprise a plurality of third actuatable devices respectively coupled to the plurality of rolling elements, wherein each third actuatable device has a first configuration in which the corresponding rolling element does not contact the surface of the airfoil-shaped body and a second configuration in which the corresponding rolling element contacts the surface of the airfoil-shaped body, wherein each third actuatable device is capable of changing its configuration from the first configuration to the second configuration in response to receipt of a fifth device actuation signal and changing its configuration from the second configuration to the first configuration in response to receipt of a sixth device actuation signal, the base of the chassis being movable by rolling on the rolling elements when the first actuatable device is in its first configuration and the third actuatable devices are in their second configuration, and the base of the chassis being not movable by rolling on the rolling elements when the first actuatable device is in its second configuration and the third actuatable devices are in their first configuration, wherein the computer system is further configured to perform the following operations: after operation (b) and before operation (e), sending the sixth device actuation signal to each of the third actuatable devices; and after operation (e) and before operation (g), sending the fifth device actuation signal to each of the third actuatable devices. In accordance with some embodiments, the rolling elements comprise balls, the first actuatable device comprises a suction cup, the second actuatable device comprises an extendible/retractable foot, and each third actuatable device comprises a respective electromechanical solenoid having an extendible/retractable element connected to a respective socket that supports a respective ball.

Other aspects of a self-propelling automated apparatus for performing a non-destructive inspection of the root, length and tip of an airfoil-shaped body using an articulated arm are disclosed below.

BRIEF DESCRIPTION OF THE DRAWINGS

The features, functions and advantages discussed in the preceding section can be achieved independently in various embodiments or may be combined in yet other embodiments. Various embodiments will be hereinafter described with reference to drawings for the purpose of illustrating the above-described and other aspects.

FIG. 3 is a diagram representing an isometric view of the articulated robot depicted in FIG. 1, positioned and configured for inspecting a portion of a tip (i.e., distal end) of the airfoil-shaped body.

FIG. 4 is a diagram representing an isometric view of some components of an articulated robot in accordance with a second embodiment. This articulated robot has a base attached to a guide chassis that is rollable in a spanwise direction along an airfoil-shaped body and further has an end effector for non-destructive inspection of the airfoil-shaped body.

Figure 1:
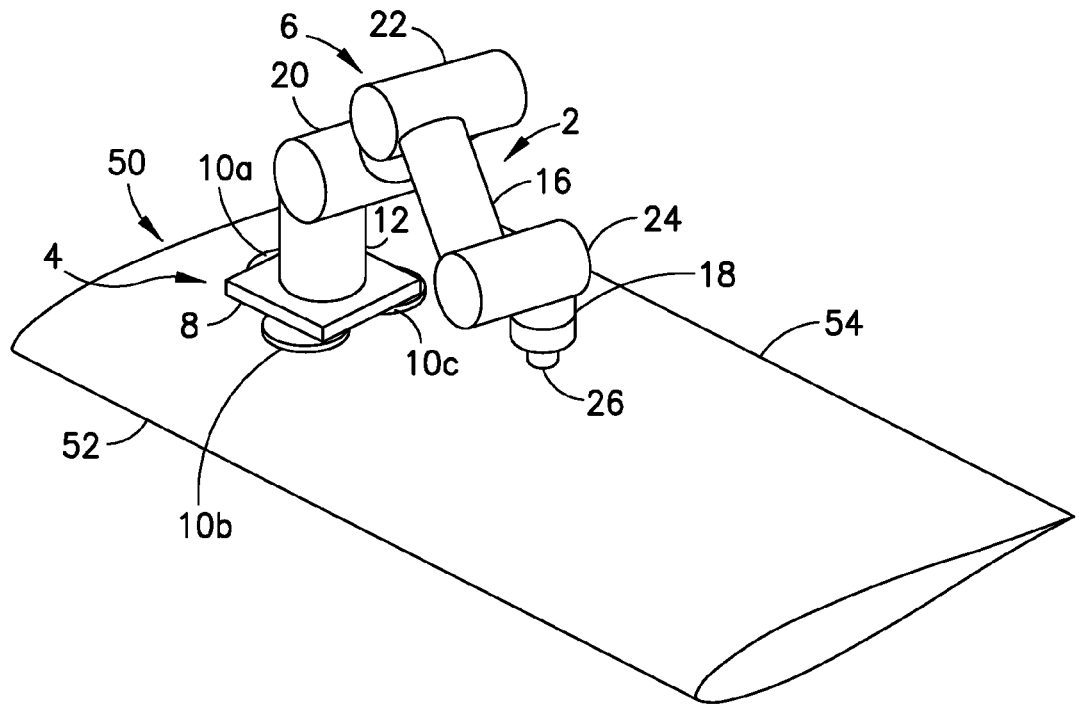
FIG. 1 is a diagram representing an isometric view of some components of an articulated robot in accordance with a first embodiment having a base adhered to a surface of an airfoil-shaped body by means of suction cups and having an end effector for non-destructive inspection of the airfoil-shaped body.

Each figure shown in this disclosure shows a variation of an aspect of the embodiments presented, and only differences will be discussed in detail.

Reference will hereinafter be made to the drawings in which similar elements in different drawings bear the same reference numerals.

DETAILED DESCRIPTION

Illustrative embodiments of a self-propelling robotic apparatus for non-destructive inspection of airfoil-shaped bodies are described in some detail below. However, not all features of an actual implementation are described in this specification. A person skilled in the art will appreciate that in the development of any such actual embodiment, numerous implementation-specific decisions may be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

FIG. 1 shows some components of an articulated robot 2 in accordance with a first embodiment having a base 8 adhered to a surface of an airfoil-shaped body 50 by means of three suction cups 10a, 10b and 10c and having an end effector 26 for non-destructive inspection of the airfoil-shaped body 50. The base 8 and suction cups 10a-10c will be referred to herein as sled chassis 4. The respective centers of the three suction cups 10a-10c are positioned at respective vertices of a hypothetical triangle.

The articulated robot 2 depicted in FIG. 1 further comprises an articulated arm 6. Articulated arms (often referred to as "manipulators") are well known in the art. For the purpose of illustration, a particular embodiment of an articulated arm 6 will now be described. However, it should be appreciated that articulated arms suitable for conducting the NDI operations disclosed herein may have a number of links and a number of joints different than what the articulated arm 6 shown in FIG. 1 has.

The articulated arm 6 (represented at a high level in FIG. 1) has six degrees of freedom. The articulated arm 6 comprises a rotary head 12 which is coupled to the base 8 by means of a "waist" twist joint (not shown) that allows the rotary head 12 to rotate about its own axis. The articulated arm 6 further comprises: a lower arm 14 (best seen in FIG. 2A) having a proximal end coupled to a distal end of the rotary head 12 by means of a "shoulder" rotary joint 20; an upper arm 16 having a proximal end coupled to a distal end of the lower arm 14 by means of an "elbow" rotary joint 22; a wrist 18 having a proximal end coupled to a distal end of the upper arm 16 by means of a "wrist roll" rotary joint 24; and an end effector 26 coupled to the wrist 18 by means of additional "wrist pitch/yaw" and "wrist twist" rotary joints (not shown in FIG. 1). For example, the end effector may be attached to a tool adapter flange that is rotatably coupled to the wrist 18 by the aforementioned "wrist twist" rotary joint, while the "wrist pitch/yaw" rotary joint may be disposed within the wrist 18.

In accordance with the embodiment depicted in FIG. 1, the end effector 26 may be any one of a multiplicity of non-destructive inspection units for inspecting the airfoil-shaped body 50 (such as a rotorcraft blade, an aircraft propeller, a small winglet, or a narrow tail section). The airfoil-shaped body 50 has a leading edge 52 and a trailing edge 54, as seen in FIG. 1, and a root 56 and a tip 58, as seen in FIG. 3.

Referring again to FIG. 1, the sled chassis 4 is movable in a spanwise direction along the surface of the airfoil-shaped body 50. The sled chassis is typically moved in increments. After each incremental movement, the sled chassis 4 can be stabilized by evacuating the space beneath the suction cups 10a-10c. While the articulated robot 2 is stationary, the articulated arm 6 can be operated to inspect any area on the surface of the airfoil-shaped body 50 within the range of motion of the articulated arm 6.

Figure 2A:
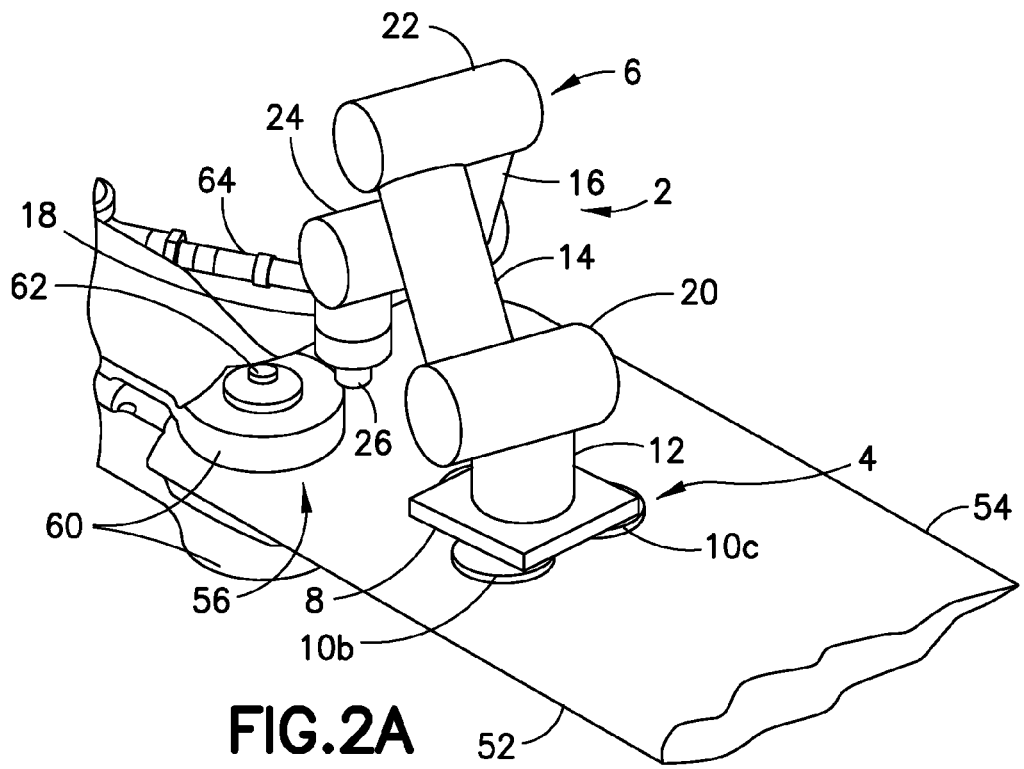
FIG. 2A is a diagram representing an isometric view of the articulated robot depicted in FIG. 1, positioned and configured for inspecting a portion of a root (i.e., proximal end) of the airfoil-shaped body.
Figure 2B:
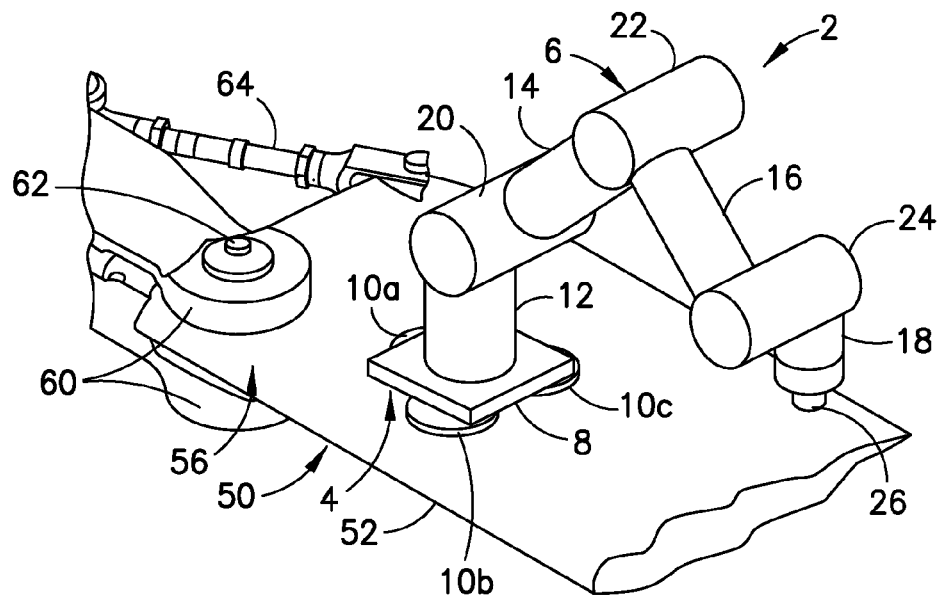
FIG. 2B is a diagram representing an isometric view of the articulated robot depicted in FIG. 1, positioned and configured for inspecting a portion of the airfoil-shaped body near a trailing edge.
Figure 2C:
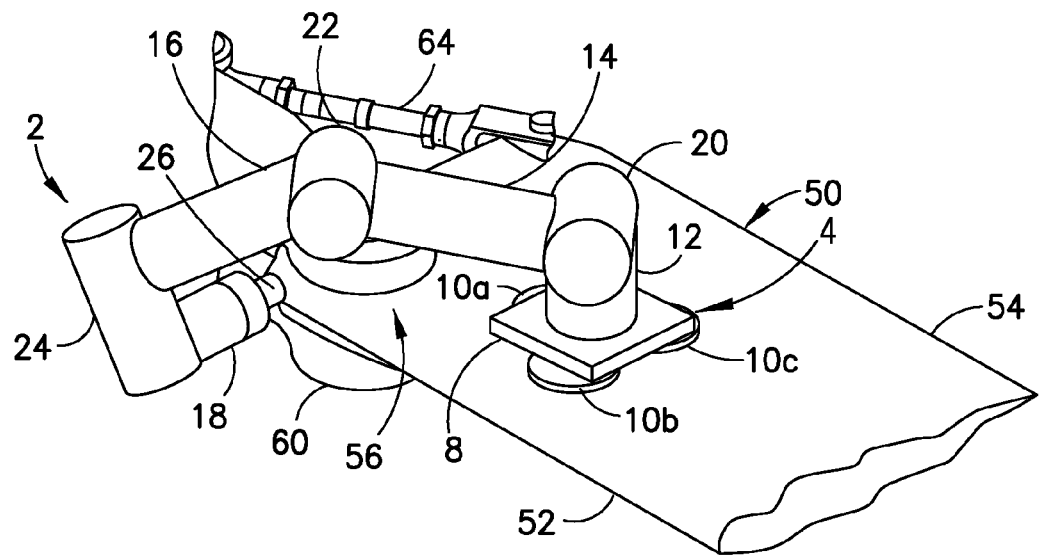
FIG. 2C is a diagram representing an isometric view of the articulated robot depicted in FIG. 1, positioned and configured for inspecting a leading edge portion of a root of the airfoil-shaped body.

FIG. 2A shows the sled chassis 4 at a first position, with the articulated arm 6 configured so that the end effector 26 is at a second position directly opposing a portion of root 56 of airfoil-shaped body 50 adjacent a blade grip 60. One end of the blade grip 60 is coupled to the airfoil-shaped body 50 by means of an attachment pin 62. The other end (not shown in FIG. 2A) of blade grip 60 is typically hinged to the rotor head (not shown) of a helicopter in such a manner that the airfoil-shaped body 50 has limited motion up and down and also can change the pitch (angle of incidence) using the control link 64. FIG. 2B shows the sled chassis 4 still in the first position, but now the articulated arm 6 has been configured so that the end effector 26 is at a third position opposing a portion of airfoil-shaped body 50 located away from the root 56. FIG. 2C shows the sled chassis 4 in the first position, but now the articulated arm 6 has been operated so that the end effector 26 is at a fourth position for interrogating a leading edge portion of root 56 of the airfoil-shaped body 50.

Thus it can be seen that, for any specific position of the sled chassis 4, the articulated robot 2 is capable of inspecting all portions of the airfoil-shaped body 50 located within reach of the articulated arm 6. The sled chassis can be initially placed at a position suitable for inspecting the root 56 of the airfoil-shaped body 50, such as the position shown in FIGS. 2A-2C. Then the sled chassis 4 can be moved in a spanwise direction by a specified distance that should be less than twice the maximum reach distance of the articulated arm 6. In that new position, the articulated robot 2 can be used to inspect an intermediate portion of the airfoil-shaped body 50. This process can be repeated until the sled chassis 4 reaches a position where the tip 58 of the airfoil-shaped body 50 can be inspected, as depicted in FIG. 3.

Figure 9:
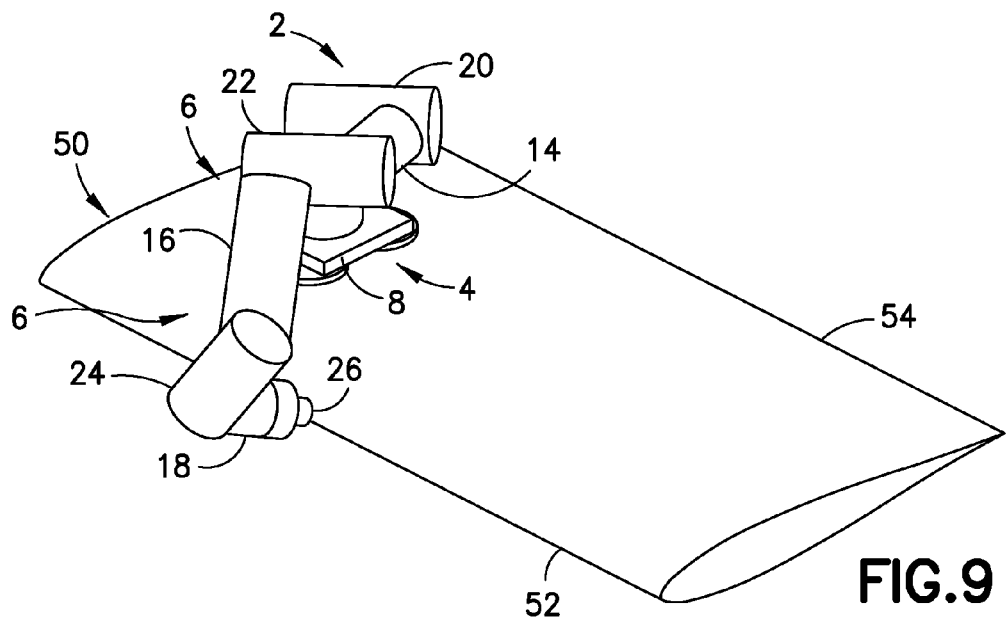
FIG. 9 is a diagram representing an isometric view of the articulated robot depicted in FIG. 1, positioned and configured for inspecting a leading edge portion of the airfoil-shaped body.

As seen in FIG. 9, the articulated robot 2 can also be positioned and configured for inspecting an intermediate portion of the leading edge 52 of the airfoil-shaped body 50.

All of the scanning tasks shown in FIGS. 2A-2C, 3 and 9 would be difficult to accomplish using a bridge that moves in a spanwise direction and an end effector that moves only in a chordwise direction along the length of the bridge because scans would need to be done on both sides of the bridge and in complex areas such as the tip and root of the airfoil-shaped body.

FIG. 4 is a diagram representing an isometric view of some components of an articulated robot 2 in accordance with a second embodiment. This articulated robot 2 has a base 8 attached to a guide chassis 28 that is rollable in a spanwise direction along an airfoil-shaped body 50 and further has an end effector 26 for non-destructive inspection of the airfoil-shaped body 50. Again, the end effector 26 may be any one of a multiplicity of non-destructive inspection units for inspecting the airfoil-shaped body 50. The guide chassis 28 is designed to travel in a spanwise direction using the airfoil-shaped body 50 as a track. The articulated robot 2 can be operated to move the end effector 26 to positions on either side of the guide chassis 28.

In accordance with the embodiment depicted in FIG. 4, the guide chassis 28 comprises a frame and a multiplicity of ball-and-socket bearings, attached to the frame. which enable the frame to roll along the airfoil-shaped body 50. The frame comprises a first pair of generally mutually parallel horizontal members 30 and 32 which connect a second pair of generally mutually parallel horizontal members 34 and 36 to form a generally rectangular upper frame portion. Opposite sides of the robot base 8 are respectively attached to members 30 and 32 respectively so that the articulated robot 2 is carried by the guide chassis 28. The guide chassis frame further comprises a vertical member 38 and a horizontal member 40. The vertical member 38 has one end connected to an intermediate portion of the horizontal member 34 and another end connected to an intermediate portion of the horizontal member 40. Ball-and-socket bearings 42a and 42b are respectively attached to opposite ends of horizontal member 40, while. ball-and-socket bearings 42c and 42d are respectively attached to the horizontal members 30 and 32 of the upper frame portion. One or more additional ball-and-socket bearings can be attached to the upper frame portion in the area of horizontal member 36.

In addition, a roller (not shown in FIG. 4) may be attached to the guide chassis frame such that the surface of the roller engages and rolls along the trailing edge 54 of the airfoil-shaped body 50. The axis of rotation of such a roller may be generally vertical. The use of a roller that bears against the trailing edge 54 of the airfoil-shaped body 50, when used in conjunction with the multiplicity of ball-and-socket bearings 42a-42d in the area of the leading edge 52 of the airfoil-shaped body 50, would oppose any tendency on the part of the guide chassis 28 to displace in the forward chordwise direction relative to the airfoil-shaped body 50. As disclosed in U.S. Published Patent Application No. 2013/0289766, such a roller may take the form of a follower encoder wheel mounted to the guide chassis frame. The spanwise position of the guide chassis 28 can be measured by a rotary encoder which encodes rotation of the encoder wheel. The encoder wheel rides on the surface of the airfoil-shaped body 50 as the guide chassis 28 travels in the spanwise direction. The rotary encoder sends respective encoder pulses to an operations control center (e.g., via an encoder cable or a wireless connection) after each incremental movement of the guide chassis 28 in the spanwise direction. Thus the spanwise coordinate of the position of guide chassis 28 can be determined.

In addition, the articulated robot 2 has encoders which enable a determination of the position coordinates of the end effector 26 in the frame of reference of the guide chassis 28 in a well-known manner. Knowing the position of the end effector 26 relative to the guide chassis 28 and the position of the guide chassis 28 relative to the airfoil-shaped body 50, the spanwise and chordwise position coordinates of the end effector 26 in the frame of reference of the airfoil-shaped body 50 can be determined.

Figure 5:
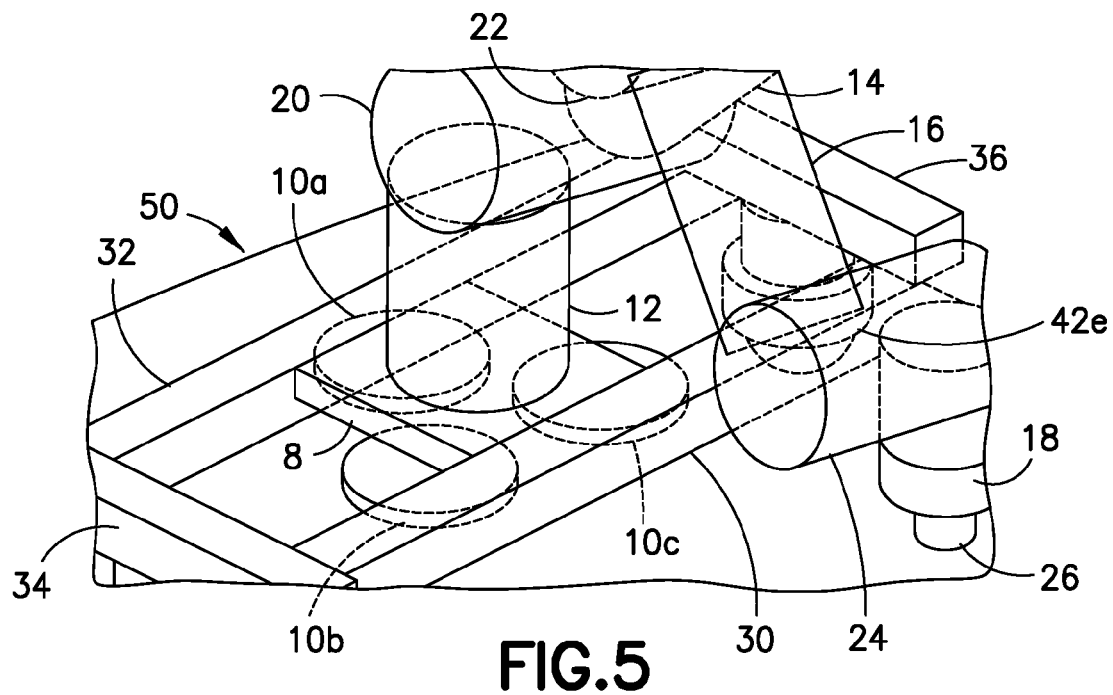
FIG. 5 is a diagram representing a magnified view of a portion of the isometric view presented in FIG. 4. This magnified view shows the robot base equipped with three suction cups for stabilizing the articulated robot during an NDI operation.

FIG. 5 presents a magnified view of a portion of the apparatus depicted in FIG. 4. This magnified view shows the robot base 8 equipped with three suction cups 10a-10c for stabilizing the articulated robot 2 during an NDI operation. Each suction cup may have a seal along its perimeter. When the space underneath a suction cup is evacuated, the suction cup will exert a suction force on the surface of the airfoil-shaped body 50 that resists movement of the guide chassis 28 relative to the airfoil-shaped body 50. The suction cups 10a-10c and the subsystem that evacuates the suction cups should be designed to produce sufficient force to stabilize (i.e., prevent movement of) the guide chassis 28 while the articulated robot 2 scans the areas on opposite sides of the guide chassis 28 in sequence.

Figure 6:
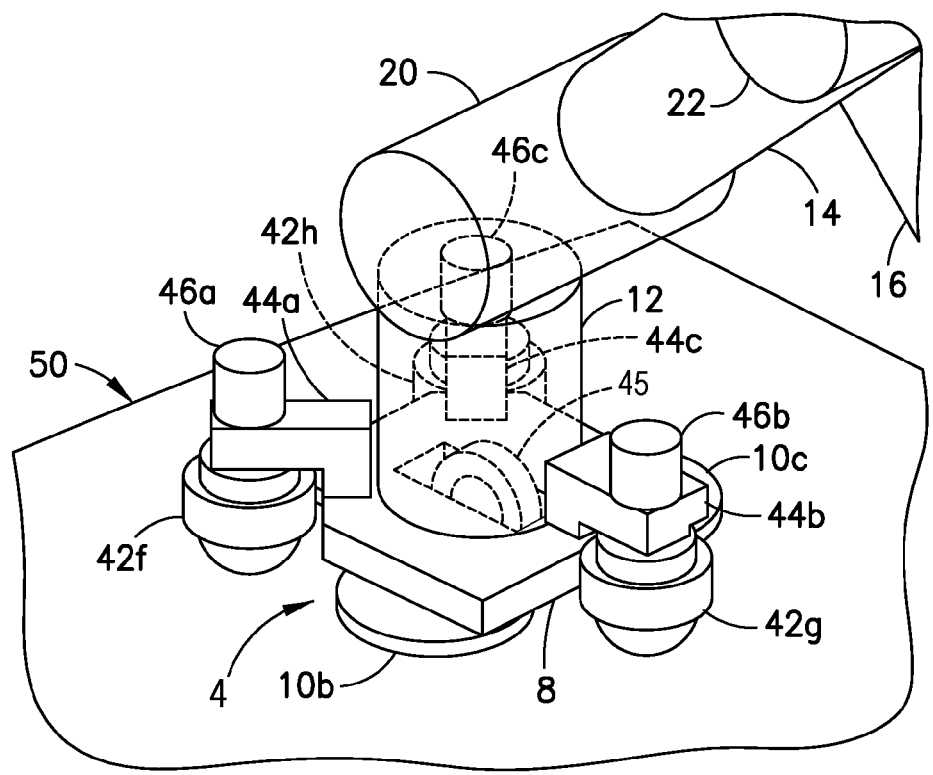
FIG. 6 is a diagram representing an isometric view of some components of an articulated robot having a base equipped with suction cups for adherence to an airfoil-shaped body, and ball-and-socket bearings and a linear roller for enabling movement along the airfoil-shaped body in accordance with a third embodiment.

FIG. 6 shows an isometric view of some components of an articulated robot 2 having a base 8 equipped with three suction cups (only suction cups 10b and 10c are visible in FIG. 6), three ball-and-socket bearings 42f-42h, and a linear roller 45 for enabling movement along the airfoil-shaped body 50 in accordance with a third embodiment. Each of the ball-and-socket bearings 42f-42h is mounted to the end of an extendible/retractable plunger (not shown) of a respective one of three electromechanical solenoids 46a-46c, which in turn are supported by a respective one of three cantilever beams 44a-44c connected to and extending from the robot base 8. The electromechanical solenoids are used to actuate engagement of the ball-and-socket bearings 42f-42h with the surface of the airfoil-shaped body 50. In alternative embodiments, other types of actuators for extending/retracting the ball-and-socket bearings 42f-42h can be utilized. During stabilization of the robot base 8, the suction cups 10*a*-10*c* are evacuated while the ball-and-socket bearings 42*f*-42*h* are retracted. Conversely, to enable movement of the robot base 8, the suction cups 10*a*-10*c* are released and the ball-and-socket bearings 42*f*-42*h* are extended so that the balls contact the surface of the airfoil-shaped body 50, allowing the robot base 8 to roll.

Still referring to FIG. 6, the linear roller 45 keeps the sled chassis 4 tracking straight during movement in the spanwise direction along the airfoil-shaped body 50. In addition, linear roller 45 may be an encoder wheel of the type previously described, outputting pulses that can be processed by a computer system to track the position of the robot base 8 in the frame of reference of the airfoil-shaped body 50.

Figure 7:
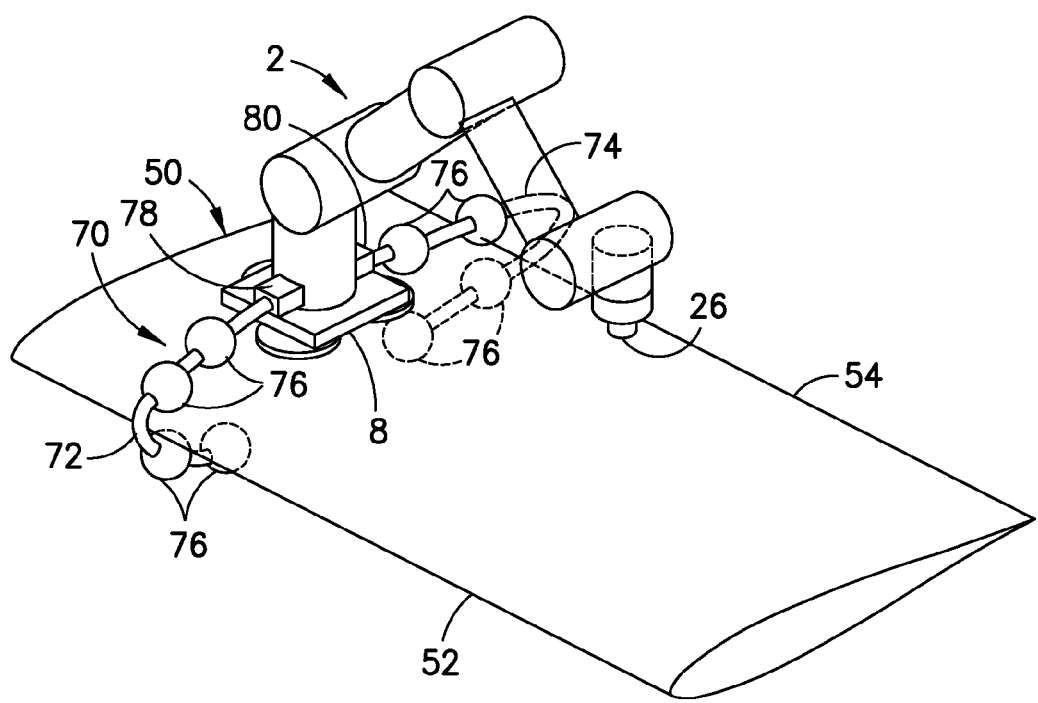
FIG. 7 is a diagram representing an isometric view of some components of an articulated robot being held on an airfoil-shaped body in part by a ball roller safety catch in accordance with a fourth embodiment.

FIG. 7 shows components of an articulated robot 2 that is being held on an airfoil-shaped body 50 in part by a ball roller safety catch 70 in accordance with a fourth embodiment. The ball roller safety catch 70 comprises a first curved axial member 72 having one end connected to a first support block 78 and a second curved axial member 74 having one end connected to a second support block 80, the first and second support blocks 78 and 80 in turn being attached to the robot base 8. The ball roller safety catch 70 further comprises a multiplicity of ball rollers 76 rotatably coupled to one or the other of the curved axial members 72 and 74 at spaced intervals therealong. The ball rollers 76 keep the robot base 8 oriented relative to the airfoil-shaped body 50, while preventing the articulated robot 8 from falling off the airfoil-shaped body 50.

Figure 8:
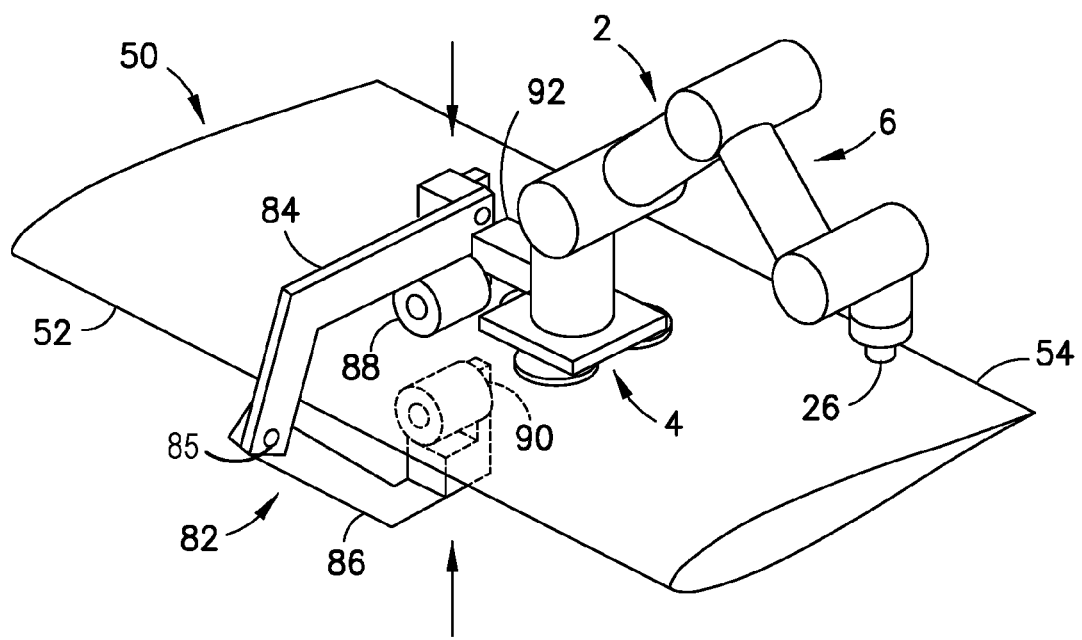
FIG. 8 is a diagram representing an isometric view of some components of an articulated robot being held on an airfoil-shaped body in part by a clamping mechanism in accordance with a fifth embodiment.

FIG. 8 shows a spring-loaded clamp mechanism 82 that can be used for stabilization of the articulated robot 8 during scanning or as a failsafe brake in accordance with a fifth embodiment. The clamp mechanism 82 comprises an upper clamp arm 84 and a lower clamp arm 86. Each of these clamp arms has a proximal end and a distal end. The proximal end of the upper clamp arm 84 is pivotably coupled to the proximal end of the lower clamp arm 86 at a pivot point 85 (e.g., a revolute joint), and the distal end of the upper clamp arm 84 is attached to the robot base 8. The clamp mechanism 82 further comprises an upper roller 88 rotatably coupled to a distal end of the upper clamp arm 84 and a lower roller 90 rotatably coupled to a distal end of the lower clamp arm 86. The upper and lower rollers 88 and 90 preferably have mutually parallel axes of rotation. The upper clamp arm 84 of the clamp mechanism 82 is connected to the sled chassis 4 by means of a cantilever beam 92.

A clamping force (indicated by opposing vertical arrows in FIG. 8) can be provided between the upper and lower clamp arms 84 and 86 that pulls them together (i.e., the clamp mechanism contracts). This clamping force could be generated by a motorized expansion/contraction rod (not shown in FIG. 8, but see FIG. 14) connecting the clamp arms at a position between the pivot point 85 and the leading edge of the airfoil-shaped body 50. In the alternative, an electro-mechanical solenoid could be used to expand or contract the clamp mechanism.

The upper and lower rollers 88 and 90 can be made of elastomeric material, providing a secure coupling of the clamp mechanism 82 to the airfoil-shaped body 50 without causing damage while the clamping force is being applied. Spring-loaded end effectors can be provided which each contain a friction brake (not shown in FIG. 8, but see FIG. 14) that bears against the outer circumferential surfaces of the upper and lower elastomeric rollers 88 and 90 under load. Under a pre-selected load, the rollers are stopped, and can no longer roll, due to the friction pads being pressed against them. A load sensor (not shown in FIG. 8, but see FIG. 14) can be provided on one of the clamp arms to provide feedback to control the loading of the clamp mechanism, to prevent over-loading. In alternative embodiments, elastomeric pads can be substituted for the elastomeric wheels, in which case clamp loading (in combination with the total suction force produced by evacuated suction cups 10*a*-10*c* or alone) may provide sufficient friction to stabilize the robot base 8.

Various means for coupling an articulated robot 2 to an airfoil-shaped body 50 for the purpose of performing non-destructive inspection have been described. In addition, means are provided for enabling the articulated robot 2 to move by self-propulsion.

Figure 10:
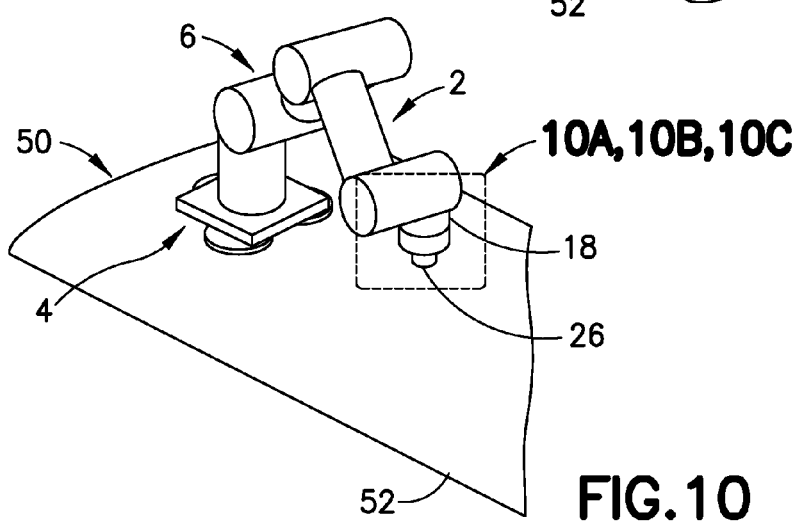
FIG. 10 is a diagram representing an isometric view of the articulated robot depicted in FIG. 1, positioned and configured at the start of a locomotion sequence.
Figure 10A:
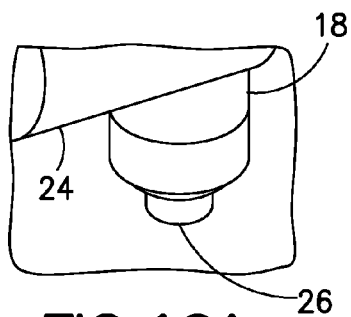
FIGS. 10A through 10C are diagrams representing isometric views of the articulated robot depicted in FIG. 10 in respective states: (1) with a friction foot retracted and the end effector exposed (FIG. 10A); (2) with the friction foot partly extended (FIG. 10B); and (3) with the friction foot fully extended beyond the end effector (FIG. 10C).
Figure 10B:
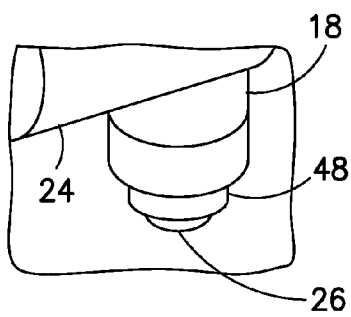
Figure 10C:
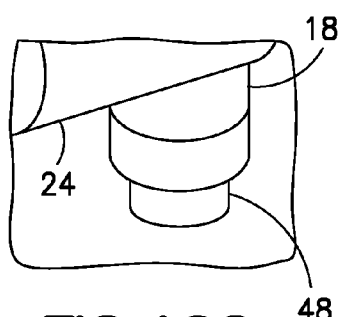

FIG. 10 represents an isometric view of the articulated robot 2 depicted in FIG. 1, positioned and configured at the start of an autonomous robot locomotion sequence. To enable self-propulsion, an extendible/retractable friction foot is coupled to the distal end of the articulated robot 2. FIGS. 10A through 10C are diagrams representing isometric views of the articulated robot 2 depicted in FIG. 10 in respective states: (1) with the friction foot retracted (not visible in FIG. 10A) and the end effector 26 exposed; (2) with the friction foot 48 partly extended (shown in FIG. 10B); and (3) with the friction foot 48 fully extended slightly beyond the end effector (shown in FIG. 10C). The friction foot 48 may be actuated to extend/retract by any suitable actuator, such as an electromechanical solenoid, a motor-driven lead screw or a fluid-driven piston (not shown in the drawings). The end face of the friction foot 48 may be coated with a material having a property that when in contact with the surface of the airfoil-shaped body 50, a high coefficient of friction will be produced. Therefore, in the state shown in FIG. 10C, the articulated robot 2 can be configured to press the friction foot 48 against the surface of the airfoil-shaped body 50, thereby generating a frictional force that resists movement of the distal end of the articulated robot 2 along that surface. Provided that the frictional force produced by components (wheels, rollers, ball rollers, pads) under the sled chassis 4 is less than the frictional force produced by the friction foot 48, the sled chassis 4 will move toward the stationary friction foot 48 when the articulated arm 6 is operated so that the proximal and distal ends thereof move toward each other. These features enable the articulated robot 2 to pull itself in a spanwise direction along the length of the airfoil-shaped body, as described below.

Figure 11A:
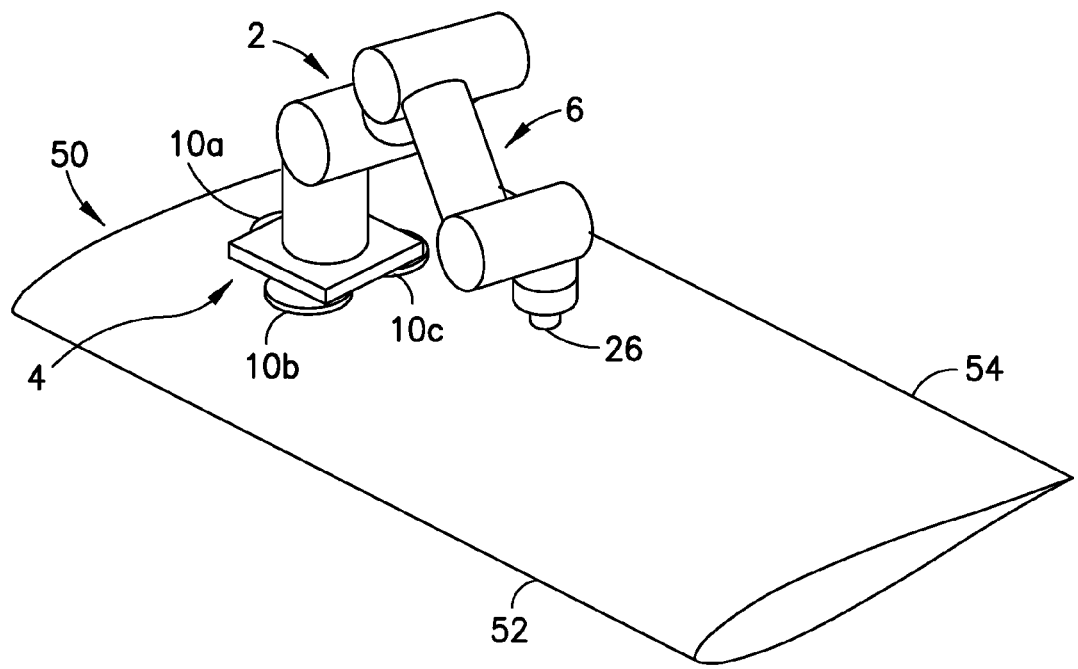
FIGS. 11A through 11F are diagrams representing isometric views of the articulated robot depicted in FIG. 1 at respective stages during a self-propelled locomotion sequence.
Figure 11B:
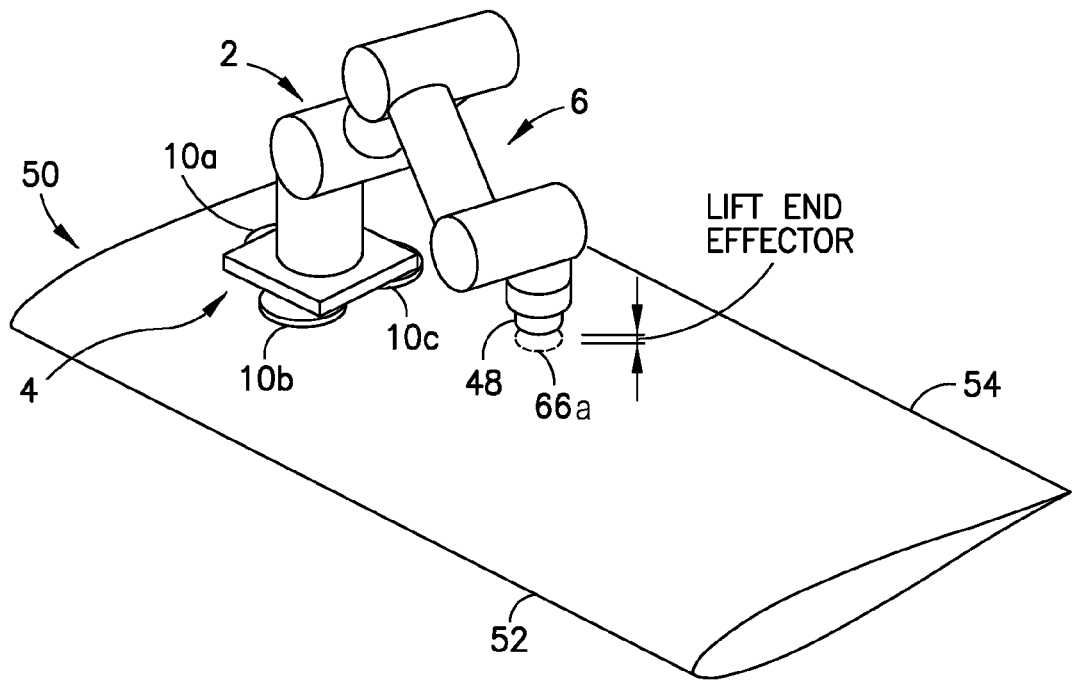
Figure 11C:
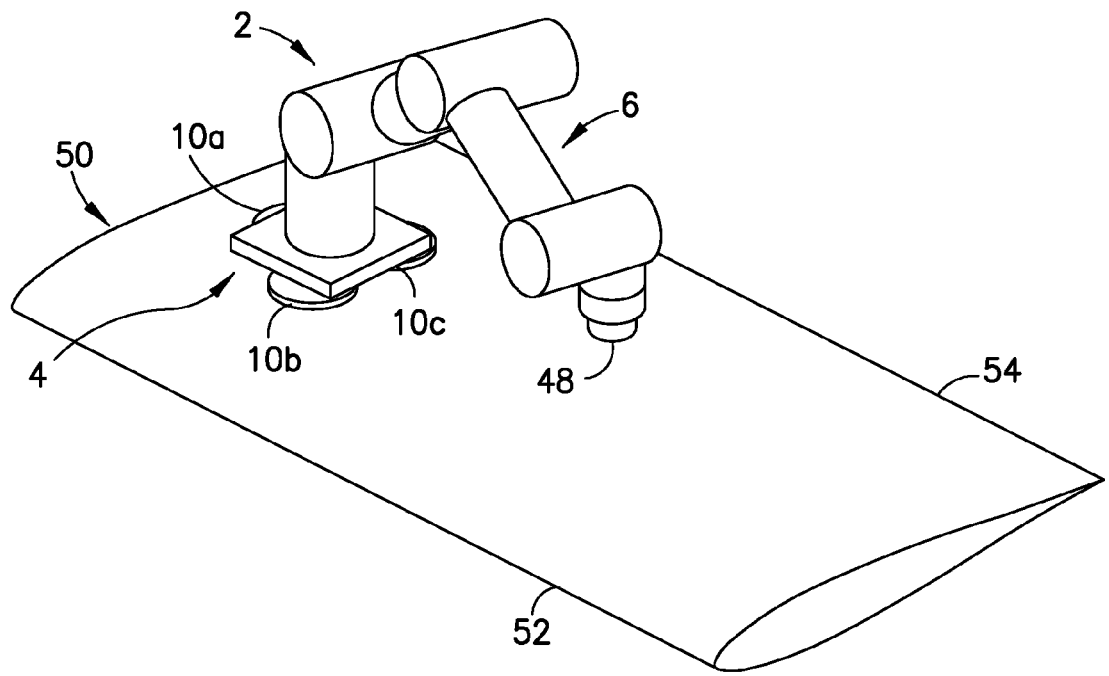
Figure 11D:
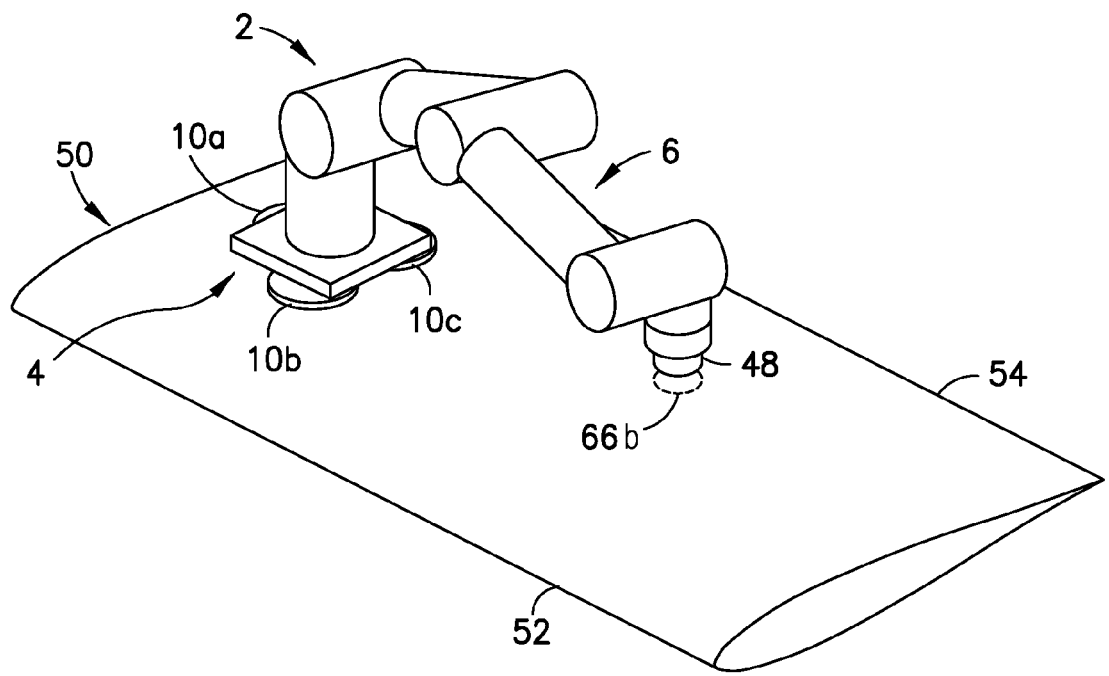
Figure 11E:
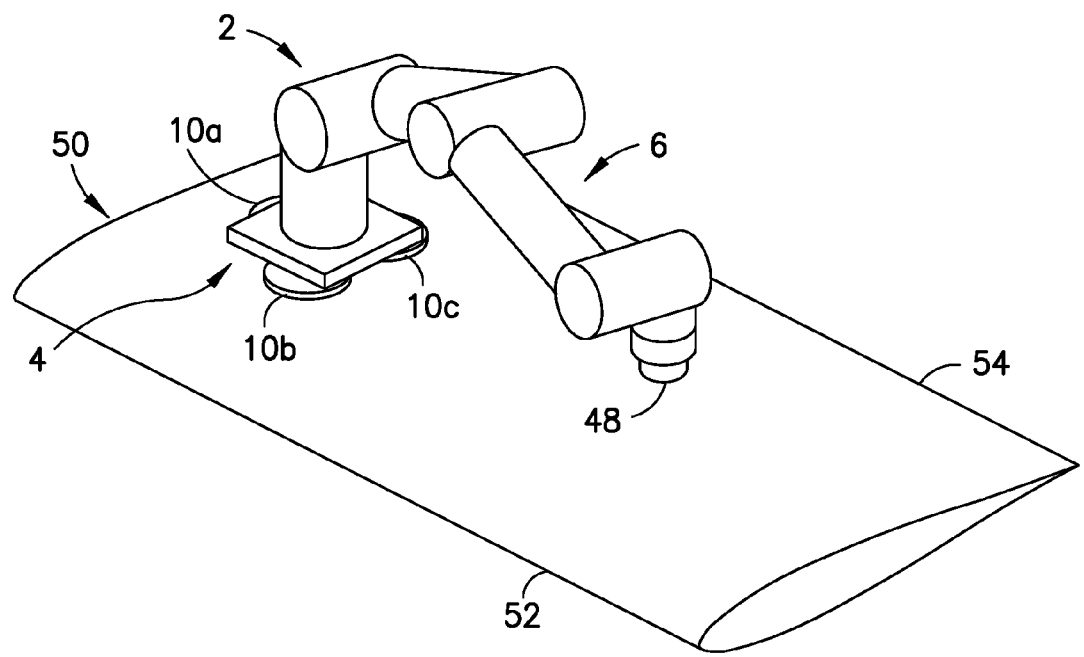
Figure 11F:
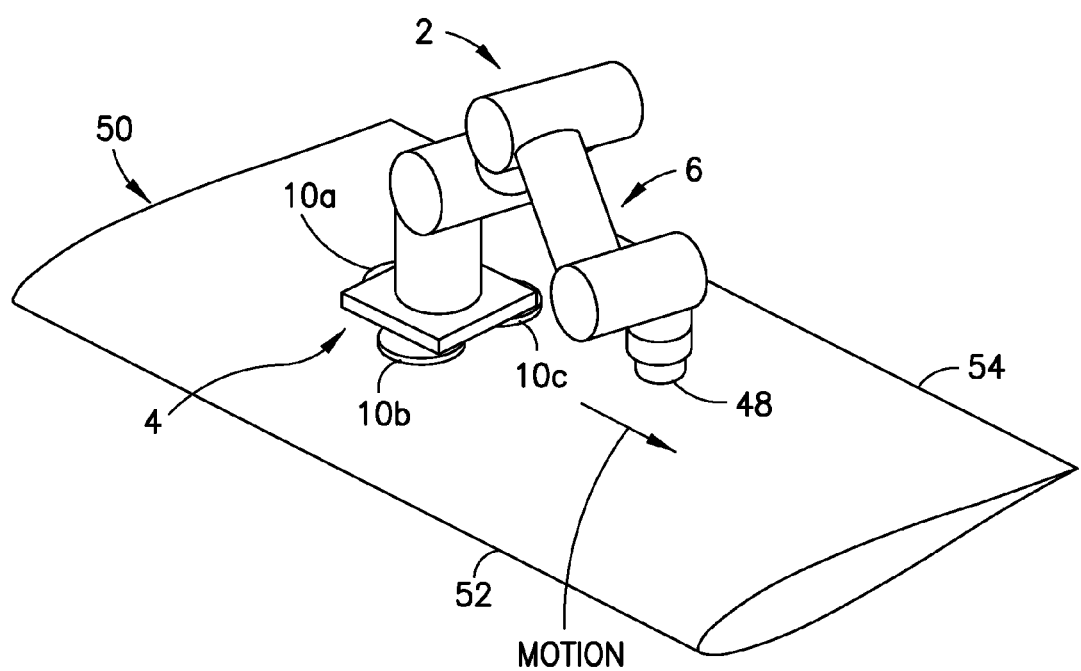

FIGS. 11A through 11F are diagrams representing isometric views of the articulated robot depicted in FIG. 1 at respective stages during a self-propelled locomotion sequence. FIG. 11A shows the articulated robot 2 in a state wherein the end effector 26 is in contact with or separated by a small gap from the surface of the airfoil-shaped body 50, which may the state upon completion of an NDI operation. In the next step, the distal end of the articulated arm 6 is lifted and the friction foot 48 is extended, as depicted in FIG. 11B. The dashed oval 66*a* in FIG. 11B represents the area of the surface of the airfoil-shaped body 50 underlying the friction foot 48 when the articulated robot is configured as shown in FIG. 11B. The configuration of the articulated robot 2 is then changed by extending the articulated arm 6, as shown in FIG. 11C. FIG. 11D shows further extension of the reach of the articulated arm 6 until the friction foot 48 overlies an area indicated by the dashed oval 66*b* in FIG. 11D. Then the distal end of the articulated arm 6 and the friction foot 48 coupled thereto are lowered until the friction foot 48 contacts the surface of the airfoil-shaped body 50, as depicted in FIG. 11E. A portion of the weight of the articulated robot 2 exerts a compression force in the area where the friction foot 48 contacts the surface of the airfoil-shaped body 50. That compressive force gives rise to a frictional force between the friction foot 48 and the surface of the airfoil-shaped body 50 that resists movement of the former along the latter. As long as the friction foot 48 has sufficiently greater friction than whatever is under the sled chassis 4 (wheels, rollers, ball rollers, pads), then the articulated arm can then be reconfigured (e.g., by rotating the upper arm relative to the rotating head, rotating the lower arm relative to the upper arm, and rotating the wrist relative to the lower arm) to pull the sled chassis 4 along the surface of the airfoil-shaped body 50 and toward the friction foot 48, as indicated by the arrow labeled "MOTION" in FIG. 11F.

Figure 12:
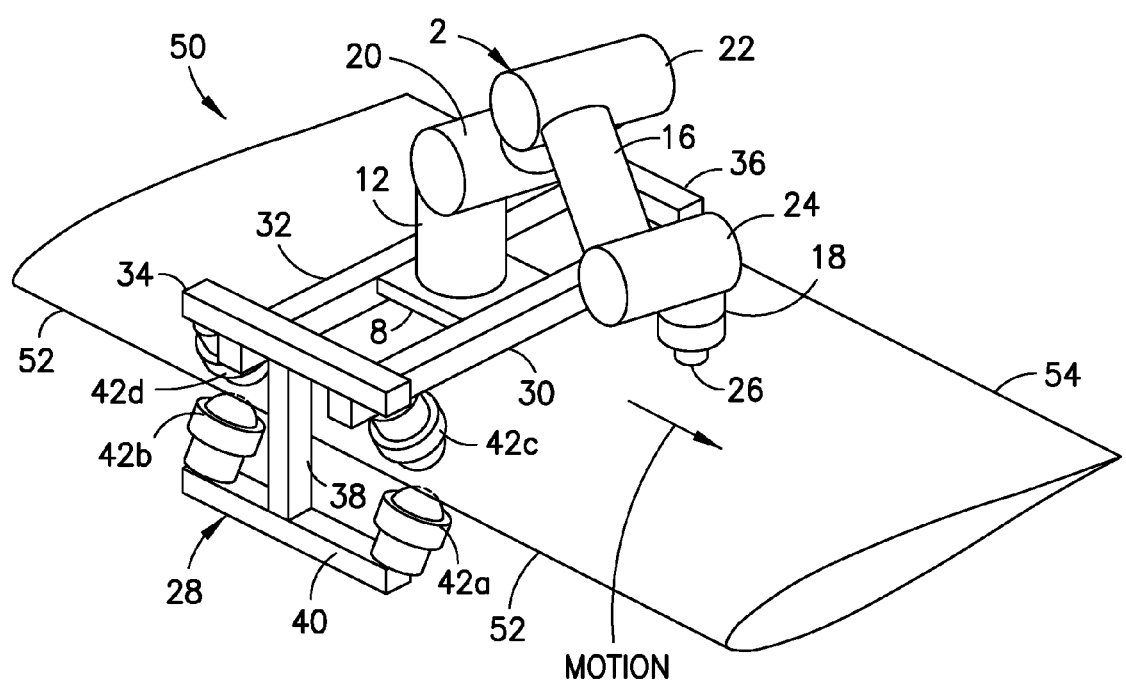
FIG. 12 is a diagram representing an isometric view of the articulated robot depicted in FIG. 4 at one stage during a self-propelled locomotion sequence.

The articulated robot 2 incorporated in the embodiment depicted in FIG. 4 may be operated in a similar manner to cause the guide chassis 28 to move, as indicated by the arrow labeled "MOTION" in FIG. 12.

Figure 13:
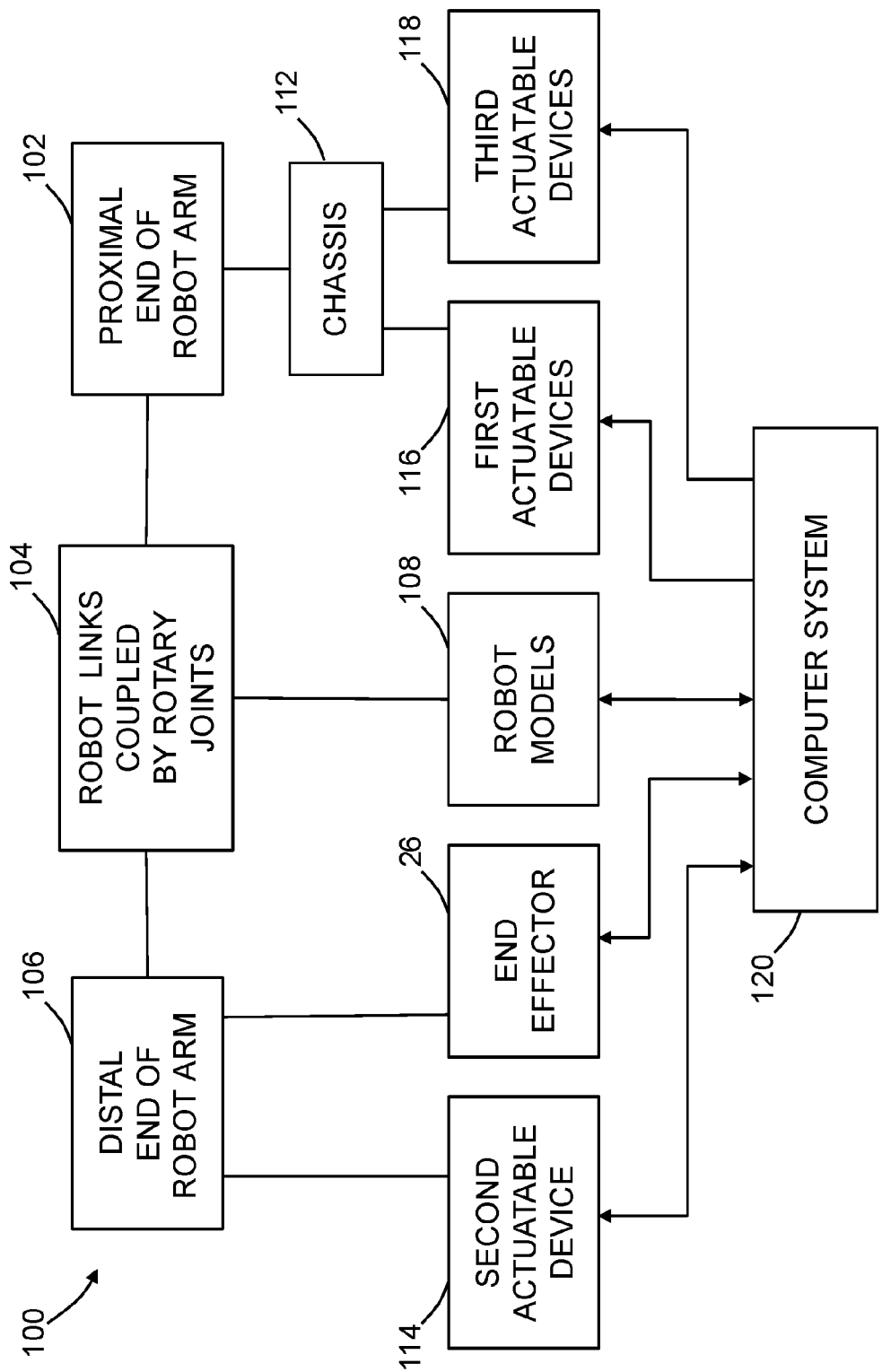
FIG. 13 is a block diagram identifying some components of a system comprising a computer-controlled articulated robot in accordance with one embodiment.

FIG. 13 is a block diagram identifying some components of a system 100 comprising a computer-controlled articulated robot in accordance with one embodiment. The robot comprises an articulated robot arm having a proximal end 102, a distal end 106, and a chain 104 of robot links coupled by rotary joints. The proximal end 102 of the robot arm is coupled to a chassis 112 comprising a base and a plurality of rolling elements coupled to the base. The rotation of the robot links at the rotary joints is driven by respective robot motors 104, which operate under the control of and send encoder pulses back to a computer system 120 (which may incorporate a data acquisition device for converting encoder pulses to digital data). The system further comprises an end effector 26 coupled to the distal end 106 of the robot arm. The end effector 26 operates under the control of and transmits acquired NDI data back to the computer system 120 (which, for example, in the case of ultrasonic inspection, may also incorporate an ultrasonic pulser/receiver unit).

The system components identified in FIG. 13 further include the following actuatable devices: (1) a plurality of first actuatable devices 116 (for example, suction cups concurrently evacuated by a valve-controlled evacuation system), coupled to the chassis 112, which can be actuated to exert a total force on the surface of the airfoil-shaped body that resists movement of the chassis 112 relative to the airfoil-shaped body; (2) a second actuatable device 114 (for example, an extendible/retractable friction foot and an associated linear actuator), coupled to the distal end 106 of the robot arm, which can be actuated to exert a force that resists movement of the distal end 106 of the robot arm relative to the airfoil-shaped body; and (3) a plurality of third actuatable devices 118 (for example, ball-and-socket bearings and associated linear actuator), coupled to the chassis 112 and to a respective one of the plurality of rolling elements of the chassis 112, which can be actuated to extend the rolling elements into contact with the surface of the airfoil-shaped body. All of these actuatable devices change their configuration in response to in response to receipt of device actuation signals from the computer system 120.

The computer system 120 is typically located at an operations command center and may communicate with the various components mentioned in the preceding two paragraphs by means of an electrical cable (not shown in the drawings). Alternatively, the computer system 120 and the articulated robot could communicate wirelessly.

In accordance with one embodiment of the system depicted at a high level in FIG. 13: the rolling elements comprise balls; the first actuatable devices comprise suction cups coupled to a valve-controlled evacuation system; the second actuatable device comprises an extendible/retractable friction foot coupled to a linear actuator, and each third actuatable device comprises an extendible/retractable ball-and-socket bearing coupled to a respective linear actuator. Different types of linear actuators can be employed to extend/retract the friction foot and the ball-and-socket bearings. For example, the linear actuators may comprise electromechanical solenoids having plungers, motor-driven lead screws or fluid-driven pistons. For the purpose of illustration, computer control of the operation of such a system will now be described in detail.

Each first actuatable device 116 has a first configuration in which the first actuatable device 116 exerts no force on a surface of an airfoil-shaped body and a second configuration in which the first actuatable device 116 exerts a force on the surface of the airfoil-shaped body that resists movement of the base of the chassis relative to the airfoil-shaped body. The first actuatable device 116 is capable of changing its configuration from the first configuration to the second configuration in response to receipt of a first device actuation signal from the computer system 120 and changing its configuration from the second configuration to the first configuration in response to receipt of a second device actuation signal from the computer system 120.

The second actuatable device 114 has a first configuration in which the second actuatable device 114 exerts no force on the surface of the airfoil-shaped body and a second configuration in which the second actuatable device 114 exerts a force on the surface of the airfoil-shaped body that resists movement of the distal end 106 of the articulated arm relative to the airfoil-shaped body. The second actuatable device 114 is capable of changing its configuration from the first configuration to the second configuration in response to receipt of a third device actuation signal from the computer system 120 and changing its configuration from the second configuration to the first configuration in response to receipt of a fourth device actuation signal from the computer system 120.

Each third actuatable device 118 has a first configuration in which the corresponding rolling element of the chassis 112 does not contact the surface of the airfoil-shaped body and a second configuration in which the corresponding rolling element contacts the surface of the airfoil-shaped body. Each third actuatable device is capable of changing its configuration from the first configuration to the second configuration in response to receipt of a fifth device actuation signal from the computer system 120 and changing its configuration from the second configuration to the first configuration in response to receipt of a sixth device actuation signal from the computer system 120.

Thus the chassis 112 is movable by rolling on the rolling elements when the first actuatable devices 116 are in their first configuration and the third actuatable devices 118 are in their second configuration, and the chassis 112 is not movable by rolling on the rolling elements when the first actuatable devices 116 are in their second configuration and the third actuatable devices 118 are in their first configuration.

In addition to movement of the chassis 112 and of the proximal end 102 of the robot arm coupled thereto, the distal end 106 of the robot arm is movable relative to the proximal end 102 in response to robot motor control signals from the computer system 120.

Finally, the end effector 26 preferably comprises a non-destructive inspection probe which is configured to perform a non-destructive inspection task in response to a probe activation signal from the computer system 120.

Bearing in mind the foregoing description of the various computer-controlled elements, the computer system 120 can be configured to perform the following operations: (a) sending the second device actuation signal to each of the first actuatable devices 116 to adhere the articulated robot to the surface of the airfoil-shaped body; (b) after operation (a), sending robot motor control signals for operating the robot motors 108 so that the distal end 106 of the robot arm moves to a position adjacent to the surface of the airfoil-shaped body at a distance from the chassis 112; (c) sending the third device actuation signal to the second actuatable device 114 to cause the friction foot 48 to extend; (d) after operation (b), sending the first device actuation signal to the first actuatable devices 116 to release the adherence force and sending the sixth device actuation signal to each of the third actuatable devices 118 to extend the ball-and-socket bearings 42f-42h; (e) after operation (d), sending robot motor control signals for operating the robot motors 108 so that the proximal end 102 of the robot arm moves toward the distal end 106; (f) after operation (e), sending the second device actuation signal to each of the first actuatable devices 116 to adhere the articulated robot to the surface of the airfoil-shaped body, sending the fourth device actuation signal to the second actuatable device 114 to cause the friction foot 48 to retract, and sending the fifth device actuation signal to each of the third actuatable devices 118 to retract the ball-and-socket bearings 42f-42h; and (g) after operations (f), sending the probe activation signal to the end effector 26 to initiate an NDI task.

Figure 14:
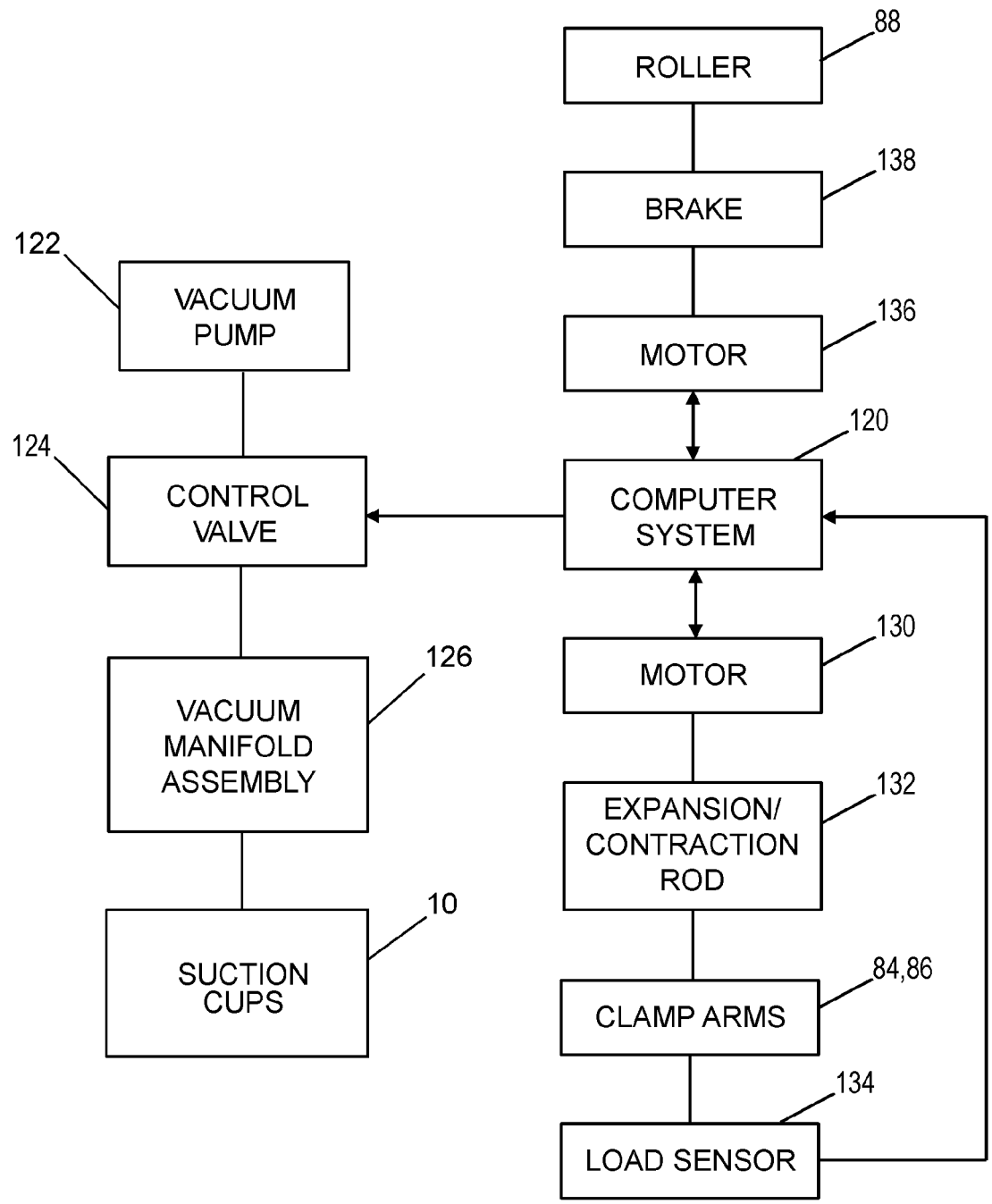
FIG. 14 is a block diagram identifying some components of a system for holding a robot base on a surface of an airfoil-shaped body using suction cups and a clamping mechanism.

FIG. 14 is a block diagram identifying some components of a system for holding a robot base on a surface of an airfoil-shaped body using a vacuum adherence system and a clamping assembly of the types partly depicted in FIG. 8. In some instances, the clamping assembly may provide sufficient stabilization of the articulated robot without the necessity of evacuating the suction cups 10. In other instances, braking of the rollers of the clamping assembly may be applied in conjunction with evacuation of the suction cups 10 to provide a greater total force to stabilize the robot base.

As seen in FIG. 14, the vacuum adherence system comprises the following components: a vacuum pump 122 which is in fluid communication with a first port of an electromechanical control valve 124: a vacuum manifold assembly 126 which is in fluid communication with a second port of the electromechanical control valve 124: and a plurality of suction cups 10 in fluid communication with the vacuum manifold assembly 126. (These components correspond to the first actuatable devices previously mentioned and recited in the claims.)

Still referring to FIG. 14, the clamping assembly comprises a pair of clamp arms 84 and 86 of the type depicted in FIG. 8. The clamp arms 84 and 86 can be rotated relative to each other by an expansion/contraction rod 132 which is driven by a motor 130. A load sensor 134 is provided on one of the clamp arms 84, 86 to provide feedback to control the loading of the clamp mechanism, to prevent over-loading. In addition, a roller 88 (coupled to the distal end of the clamp arm 84 in FIG. 8) can be provided with a brake 138 which is driven by a motor 136 to apply a baking force on the roller 88. A similar braking may exert a braking force on the roller 90 (coupled to the distal end of the clamp arm 86 in FIG. 8).

The system partly depicted in FIG. 14 further comprises a computer system 120 which is configured (i.e., programmed) to control motor 130 in dependence on load sensor data received from the load sensor 134. The computer system 120 can also be configured to selectively control the motor 136 to apply a braking force on one or both rollers 88 and 90. Both motors 130 and 136 may comprise stepper motors having internal encoders that provide encoder pulses to a data acquisition device (not shown in FIG. 14) that converts the pulses into digital data suitable for use by the computer system 120.

The computer system 120 is further configured to control the state of the control valve 124 that connects the vacuum pump 122 to the vacuum manifold assembly 126. The latter comprises a plurality of vacuum manifolds which are in fluid communication with respective suction cups 128. The computer system 120 can be programmed to send a signal that causes the control valve 124 to open. In the valve open state, the vacuum pump 122 will apply a partial vacuum to the vacuum manifold assembly 126, causing the suction cups 10 to adhere to the surface of the airfoil-shaped body 50.

The term "manifold" is used herein in the sense of a chamber or duct having several outlets through which a fluid can be distributed or gathered. These manifolds connect channels in the suction cups 128 to the vacuum system comprising vacuum pump 122 and control valve 124. The vacuum system is connected to the chassis 112 by way of an umbilical cable that may include air lines, electrical lines, and even a water line (e.g., in cases where the end effector is an ultrasonic sensor or sensor array). In accordance with alternative embodiments, each individual suction cup has a respective vacuum motor (not shown).

The computer system 120 may also be configured to control a cable management system (not shown). For example, motion control application software running on the computer system 120 can control a cable motor of the cable management system. During an inspection procedure, one or more cables need to accompany the chassis 112 down the length of the airfoil-shaped body 50, e.g., a helicopter blade. The motion control software running on the computer system 120 synchronizes the movement of the cables with the movement of the chassis 112, extending or retracting the cables as appropriate. The computer system 120 can be programmed to control the cable motor (not shown) in dependence on crawler position information derived from position sensors (not shown). In accordance with the embodiments described above, the computer system 120 is provided with information concerning the spanwise position of the chassis 112. This functionality can be provided by any one of a multiplicity of known positional tracking mechanisms.

Figure 15:
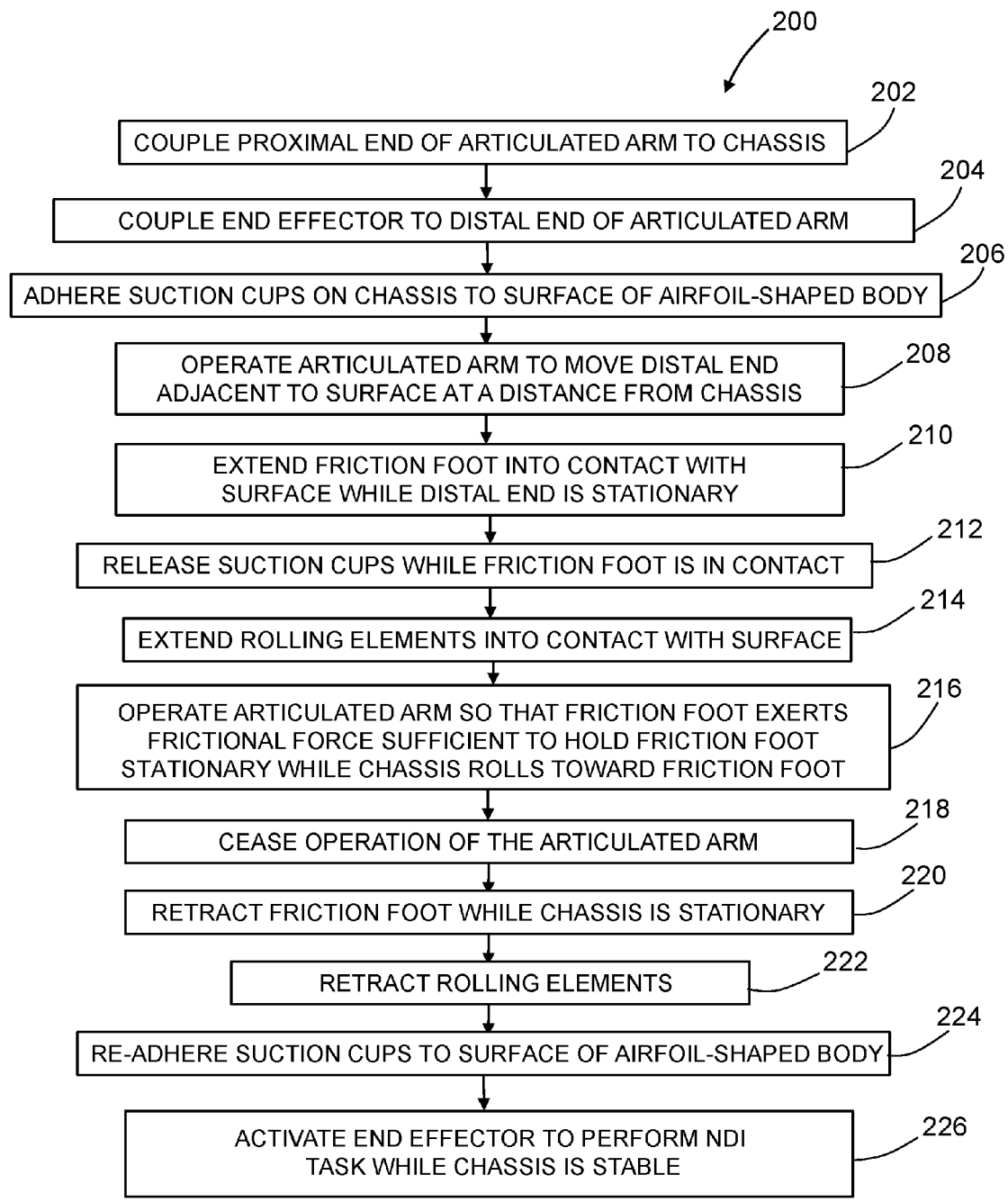
FIG. 15 is a flowchart identifying steps of a method for automated non-destructive inspection of an airfoil-shaped body in accordance with some embodiments.

To further clarify the technology disclosed herein, the flowchart in FIG. 15 identifies some of the steps of a method 200 for automated non-destructive inspection of an airfoil-shaped body in accordance with some embodiments. First, a proximal end of an articulated arm is coupled to a chassis that is equipped with a plurality of suction cups and a plurality of rolling elements (step 202). Then an end effector is coupled to a distal end of the articulated arm (step 204). Next the suction cups of the chassis are adhered to a surface of an airfoil-shaped body (step 206). At the start of a robot locomotion sequence (i.e., while the suction cups are adhered to the surface of the airfoil-shaped body), the articulated arm is operated so that its distal end moves adjacent to the surface of the airfoil-shaped body at a distance from the chassis (step 208). While the suction cups are still adhered to the surface of the airfoil-shaped body, a friction foot at the distal end of the articulated arm is extended into contact with the surface of the airfoil-shaped body (step 210). Then while the friction foot is in contact with the surface of the airfoil-shaped body, the suction cups are released (step 212). While the suction cups are released, the plurality of rolling elements are extended into contact with the surface of the airfoil-shaped body at the chassis (step 214). Then the articulated arm is operated so that the frictional force exerted by the friction foot is sufficient to hold the friction foot stationary while the chassis rolls on the rolling elements toward the friction foot (step 216). After the foregoing robot operation has ceased (step 218), the friction foot is retracted (step 220) and the plurality of rolling elements are retracted (step 222). Then the suction cups are re-adhered to the surface of the airfoil-shaped body (step 224). While the chassis is stable, the end effector is then activated to perform an NDI task (step 226).

Figure 16:
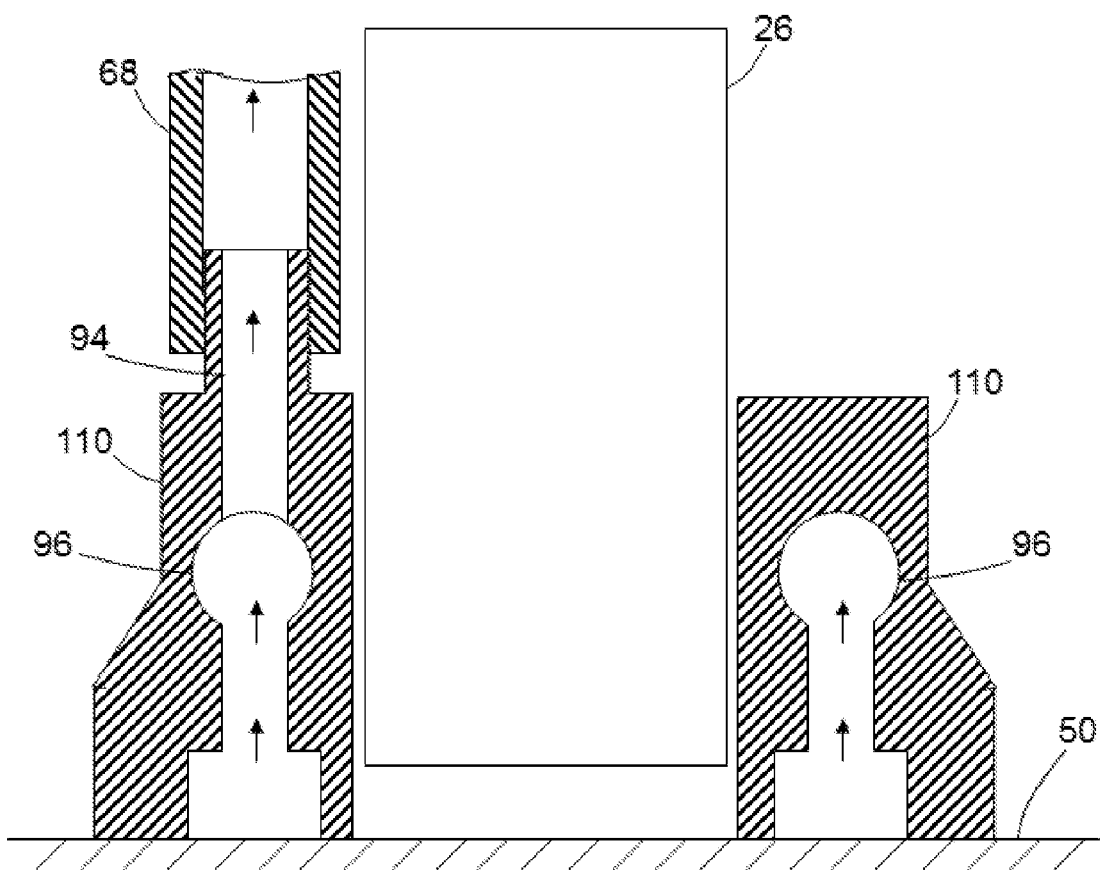
FIG. 16 is a diagram representing a partially sectioned view of a distal end of an articulated robot arm in accordance with an alternative embodiment.

In accordance with alternative embodiments, the distal end of the articulated arm may be provided with a suction foot 110 (see FIG. 16) instead of a friction foot. The suction foot 110 would be extendible/retractable between first and second positions relative to the end effector 26. In the first position (not shown in FIG. 16), the end effector 26 would be in contact with the surface of the airfoil-shaped body 50 while the suction foot 110 is separated from the surface of the airfoil-shaped body 50 by a gap. In the second position (shown in FIG. 16), the suction foot 110 would be in contact with the surface of the airfoil-shaped body 50 while the end effector 26 is separated from the surface of the airfoil-shaped body 50 by a gap.

The suction foot 110 may comprise a ring-shaped rubber cylinder having an annular vacuum manifold 96 which, when evacuated by a vacuum pump (not shown in FIG. 16), exerts a suction force capable of affixing the suction foot 110 to the surface of the airfoil-shaped body 50. The suction foot 110 further comprises a channel 94 which connects the annular vacuum manifold 96 to a hose 68 that is in turn connected to the vacuum pump by way of a control valve (not shown in FIG. 16, but see FIG. 14). In the implementation depicted in FIG. 16, the suction force is applied over an annular area of the surface of the airfoil-shaped body 50. In other implementations, individual channels in fluid communication with an internal annular vacuum manifold can exert respective individual suction forces, the total suction force being sufficient to affix the distal end of the articulated robot arm to the surface of the airfoil-shaped body 50, thereby preventing both translation and rotation of the entire apparatus on the airfoil-shaped body 50 even when the suction is removed from the suction cups 10a-10c which are attached to the robot base 8 (see FIG. 1).

In accordance with a further enhancement, the suction cups attached to the robot base 8 may comprise floating suction cups of the type disclosed in U.S. patent application Ser. No. 14/197,306. When the airflow to the floating suction cups attached to the robot base 8 is reversed, the floating suction cups would effectively function as air bearings, allowing the robot base 8 to ride on an air cushion. The entire apparatus can be now be translated by the articulated arm 6 using the distal suction foot 110 as an alternative secure base.

Figure 17A:
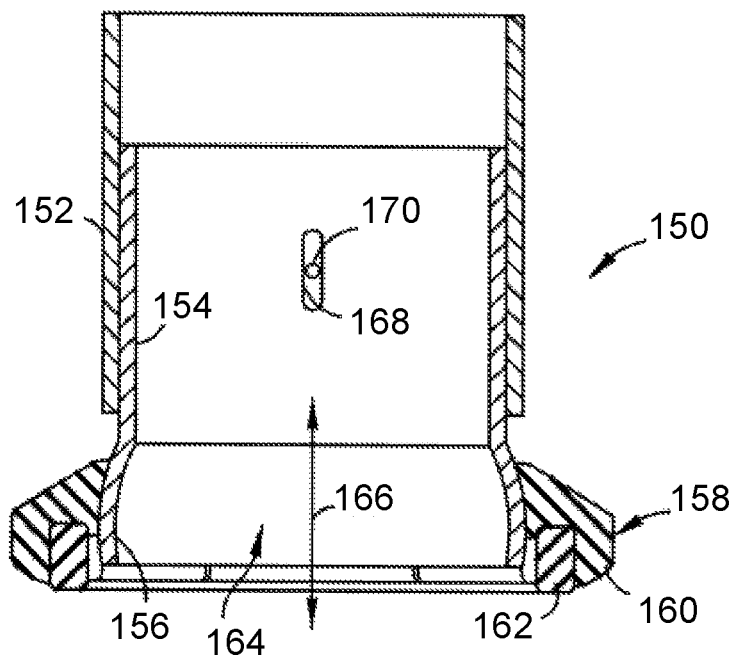
FIG. 17A is a diagram showing a cross-sectional view of a vacuum adherence device in accordance with one implementation.

In accordance with one embodiment, all of the floating suction cups attached to the robot base may have a similar structure. FIG. 17A is a diagram showing a cross-sectional view of a floating suction cup 150 in accordance with one implementation. This floating suction cup 150 comprises a circular cylindrical sleeve housing 152 and a sleeve 154 having a circular cylindrical portion which is axially slidable along a center axis 166 inside the sleeve housing 152. The sleeve 154 further comprises bearing portion 156 having an outer spherical bearing surface having a center point located along the center axis 166. The bearing portion 156 may be integrally formed with the aforementioned circular cylindrical portion of sleeve 154. The floating suction cup 150 further comprises a pivotable seal assembly 158 comprising a socket ring 160 that holds a seal 162. The socket ring 160 also has an inner spherical bearing surface which is concentric with and pivotably coupled to the outer spherical bearing surface of bearing portion 156 of sleeve 154. The pivot point of the socket ring 160 is collocated with the center point of the outer spherical bearing surface of bearing portion 156 of sleeve 154.

The pivotable seal assembly 158 is configured to rotate relative to the sleeve 154 about the pivot point to at least partially conform to a shape of a confronting surface. The floating suction cup 150 can adhere to such a confronting surface when air is drawn into a channel 164 formed in part by the channel of sleeve housing 152, in part by the channel of sleeve 154, and in part by the opening in the seal 162. The pivotable seal assembly 158 is configured to rotate relative to the sleeve 154 independently of translational movement of the sleeve 154 in a direction parallel to the center axis 66 within the sleeve housing 152. The amount of rotation of pivotable seal assembly 158 may be limited by the size and/or shape of the outer spherical bearing surface of the bearing portion 156 of sleeve 154.

Although not shown in FIG. 17A, the floating suction cup preferably comprises a spring arranged to urge the sleeve 154 to extend out of the sleeve housing 152 by downward (as seen in the view of FIG. 17A) sliding along the center axis 166. This sliding movement may be restricted to within a selected range of movement. However, sleeve 154 may "float" freely relative to sleeve housing 152 within this selected range of movement. This restriction of the translational motion of sleeve 154 can be implemented by providing a slot 168 in the wall of the circular cylindrical portion of sleeve 154 and by providing a pin 170 which extends radially inward from the wall of sleeve housing 152 and into the slot 168. The pin 170 may also be used to hold sleeve 154 inside sleeve housing 152. The length of slot 168 restricts the sliding movement of sleeve 154 relative to sleeve housing 152.

The channel 164 is in fluid communication with a control valve (not shown in FIG. 17A), which control valve is in turn in flow communication with a vacuum pump (also not shown in FIG. 17A). The vacuum pump, control valve, channel 164, and connecting conduits form a vacuum system which is configured to draw air into the channel 164 such that a vacuum adherence is formed between the pivotable seal assembly 158 and a confronting surface. The vacuum adherence is the result of a vacuum pressure generated inside the channel 164. When the flow of air is reversed, air provided by the pump flows through any gap between the seal 162 and the confronting surface of the airfoil-shaped body 50. The flow of air radially inward through such gap has the effect of producing an air cushion. The height of the gap may vary along the periphery of the seal 162. This gap height depends on the shape of the confronting surface and the degree of rotation of the seal 162 to conform to that shape.

The seal 162 may be formed of any one of a number of different materials. For example, seal 162 may comprise silicone rubber or other elastomeric material, a viscoelastomeric material, or some other suitable flexible material.

Figure 17B:
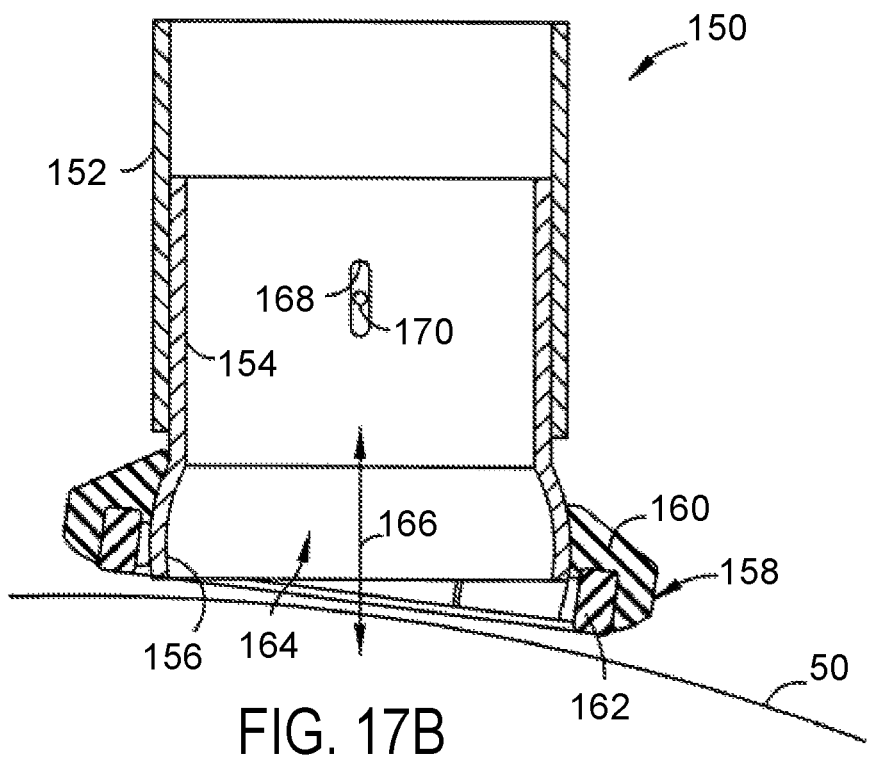
FIG. 17B is a diagram showing a cross-sectional view of the vacuum adherence device depicted in FIG. 17A adhered to a non-planar blade surface. The air gap between the vacuum adherence device and the non-planar surface has been exaggerated for the purpose of illustration.

FIG. 17B shows a cross-sectional view of the floating suction cup 150 depicted in FIG. 17A adhered to a convex curved surface of the airfoil-shaped body 50. The air gap between the floating suction cup 150 and the convex curved surface has been exaggerated for the purpose of illustration. The air gap may function as an air bearing that holds the pivotable seal assembly 158 close to the surface of airfoil-shaped body 50, while reducing static friction to within selected tolerances. In other words, the air gap allows pivotable seal assembly 158 to "float" above the surface of airfoil-shaped body 50 while maintaining vacuum adherence between pivotable seal assembly 158 and that surface 1. Further, the air gap allows pivotable seal assembly 158 to be moved over the surface with a reduced amount of static friction and without causing undesired effects to the surface.

In one embodiment, the seal 162 may be corrugated in such a way as to allow small channels for airflow between the seal 162 and the component surface. In some instances, these corrugated channels have been shown to promote vacuum on surfaces of uneven profile or varying surface roughness. In accordance with this embodiment, the corrugations may comprise a low-friction material that further induces sliding such that base motion will be enabled, yet airflow is ensured by the corrugated channels.

This apparatus and methods disclosed hereinabove enable inspection of a rotorblade root and tip, as well as the acreage and edges in the main portion of the blade. The distal end of an articulated arm robot that tracks along a rotorblade is used for NDI. The sensor can be a single probe or array. The sensor can be ultrasonic, electromagnetic, infrared thermographic, terahertz, microwave, visual, etc., or some combination thereof. Guidance and positioning can be pre-programmed or guided via a joystick, or some of both. The disclosed apparatus enables complete coverage of the rotorblade, including the relatively more geometrically complex root and tip.

While articulated robots for automated non-destructive inspection of airfoil-shaped bodies have been described with reference to particular embodiments, it will be understood by those skilled in the art that various changes may be made and equivalents may be substituted for elements thereof without departing from the scope of the teachings herein. In addition, many modifications may be made to adapt the concepts and reductions to practice disclosed herein to a particular situation. Accordingly, it is intended that the subject matter covered by the claims not be limited to the disclosed embodiments.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices comprising a processing unit (e.g., a central processing unit, an integrated circuit or an arithmetic logic unit).

The process claims set forth hereinafter should not be construed to require that the steps recited therein be performed in alphabetical order (any alphabetical ordering in the claims is used solely for the purpose of referencing previously recited steps) or in the order in which they are recited. Nor should they be construed to exclude any portions of two or more steps being performed concurrently or alternatingly.

The invention claimed is:

1. An apparatus comprising:
a chassis comprising a base, first, second and third cantilever beams connected to and extending from the base, first second and third actuators supported by the first, second and third cantilever beams respectively and comprising first second and third extendible/retractable plungers respectively, and first, second and third ball and socket bearings mounted to respective ends of the first second and third extendible/retractable plungers;
an articulated arm having a proximal end coupled to the base of the chassis and having a distal end;
a non-destructive inspection probe coupled to the distal end of the articulated arm; and
first, second and third suction cups coupled to the base of the chassis.

2. An apparatus comprising:
a chassis comprising a base and a plurality of rolling elements coupled to the base;
an articulated arm having a proximal end coupled to the base of the chassis and having a distal end;
a non-destructive inspection probe coupled to the distal end of the articulated arm;
a first suction cup coupled to the base of the chassis;
a foot coupled to the distal end of the articulated arm and surrounding a portion of said non-destructive inspection probe, wherein the foot is extendible from a retracted position to an extended position, the foot having an end extending beyond the non-destructive inspection probe when the foot is in the extended position.

3. The apparatus as recited in claim 2, wherein the rolling elements are ball rollers.

4. The apparatus as recited in claim 3, wherein the chassis further comprises a curved axial member having one end connected to the base, and a plurality of the ball rollers are rotatably mounted to the curved axial member.

5. The apparatus as recited in claim 2, wherein the foot comprises one of the following: a friction foot or a suction foot.

6. The apparatus as recited in claim 2, further comprising a plurality of actuators, each actuator being coupled to a respective one of the plurality of rolling elements for alternately extending or retracting the rolling element.

7. An apparatus comprising:
a chassis comprising a base and a plurality of rolling elements coupled to the base;
an articulated arm having a proximal end coupled to the base of the chassis and having a distal end;
a non-destructive inspection probe coupled to the distal end of the articulated arm;
first, second and third suction cups coupled to the base of the chassis, the first, second and third suction cups being arranged so that their respective centers are positioned at respective vertices of a hypothetical triangle, wherein the chassis further comprises a linear roller disposed in an area bounded by the hypothetical triangle.

8. The apparatus as recited in claim 2, wherein the chassis further comprises first and second clamp arms, each of the first and second clamp arms comprising a proximal end and a distal end, the proximal end of the first clamp arm being coupled to the proximal end of the second clamp arm, and the distal end of the first clamp arm being attached to the base, and wherein the plurality of rolling elements comprise first and second rollers disposed between and respectively supported by the distal ends of the first and second clamp arms with a gap therebetween, the first and second rollers having mutually parallel axes of rotation.

9. A method comprising:
(a) coupling a proximal end of an articulated arm to a chassis that is equipped with a plurality of suction cups and a plurality of rolling elements;
(b) coupling an end effector and an extendible foot to a distal end of the articulated arm;
(c) adhering the suction cups to a surface of an airfoil-shaped body;

(d) operating the articulated arm so that its distal end moves adjacent to the surface of the airfoil-shaped body at a distance from the chassis;
(e) extending the foot into contact with the surface of the airfoil-shaped body at the distal end of the articulated arm;
(f) releasing the suction cups;
(g) extending the plurality of rolling elements into contact with the surface of the airfoil-shaped body at the chassis; and
(h) causing the foot to exert a force sufficient to hold the foot stationary while the chassis rolls toward the foot, wherein steps (d) and (e) are performed while the suction cups are adhered to the surface of the airfoil-shaped body, step (g) is performed while the suction cups are released, and step (h) is performed while the plurality of rolling elements are in contact with the surface of the airfoil-shaped body.

10. The method as recited in claim 9, further comprising the following steps performed after step (h):
(i) retracting the foot;
(j) retracting the plurality of rolling elements;
(k) re-adhering the suction cups to the surface of the airfoil-shaped body; and
(l) activating the end effector to perform a non-destructive inspection task.

11. The method as recited in claim 10, further comprising operating the articulated arm, prior to step (l), so that the end effector moves to a position overlying a portion of the surface at an end of the airfoil-shaped body.

12. The method as recited in claim 11, wherein the end of the airfoil-shaped body is a root.

13. The method as recited in claim 11, wherein the end of the airfoil-shaped body is a tip.

14. An automated apparatus for non-destructive inspection of an airfoil-shaped body having leading and trailing edges extending from a root to a tip, comprising:
a chassis comprising a base and a plurality of rolling elements coupled to the base;
a first actuatable device coupled to the base of the chassis and having a first configuration in which the first actuatable device exerts no force on a surface of an airfoil-shaped body and a second configuration in which the first actuatable device exerts a force on the surface of the airfoil-shaped body that resists movement of the base of the chassis relative to the airfoil-shaped body, wherein the first actuatable device is capable of changing its configuration from the first configuration to the second configuration in response to receipt of a first device actuation signal and changing its configuration from the second configuration to the first configuration in response to receipt of a second device actuation signal;
an articulated arm comprising a proximal end coupled to the base of the chassis, a distal end, and a plurality of links coupled by motor-driven rotary joints to form a chain connecting the distal end to the proximal end, the distal end being movable relative to the proximal end in response to robot motor control signals;
a non-destructive inspection probe coupled to the distal end of the articulated arm and configured to perform a non-destructive inspection task in response to a probe activation signal;
a second actuatable device coupled to the distal end of the articulated arm and having a first configuration in which the second actuatable device exerts no force on the surface of the airfoil-shaped body and a second configuration in which the second actuatable device exerts a force on the surface of the airfoil-shaped body that resists movement of the distal end of the articulated arm relative to the airfoil-shaped body, wherein the second actuatable device is capable of changing its configuration from the first configuration to the second configuration in response to receipt of a third device actuation signal and changing its configuration from the second configuration to the first configuration in response to receipt of a fourth device actuation signal; and
a computer system configured to perform the following operations:
(a) sending the second device actuation signal to the first actuatable device;
(b) after operation (a), sending robot motor control signals for operating the articulated arm so that its distal end moves to a position adjacent to the surface of the airfoil-shaped body and at a distance from the chassis;
(c) sending the third device actuation signal to the second actuatable device;
(d) after operation (b), sending the first device actuation signal to the first actuatable device;
(e) after operation (d), sending robot motor control signals for operating the articulated arm so that its proximal end moves toward its distal end;
(f) after operation (e), sending the second device actuation signal to the first actuatable device and sending the fourth device actuation signal to the second actuatable device; and
(g) after operations (f), sending the probe activation signal to the non-destructive inspection probe.

15. The automated apparatus as recited in claim 14, wherein the first actuatable device comprises a suction cup, and the second actuatable device comprises an extendible/retractable foot.

16. The automated apparatus as recited in claim 15, wherein the foot comprises one of the following: a friction foot or a suction foot.

17. The automated apparatus as recited in claim 14, further comprising a plurality of third actuatable devices respectively coupled to the plurality of rolling elements, wherein each third actuatable device has a first configuration in which the corresponding rolling element does not contact the surface of the airfoil-shaped body and a second configuration in which the corresponding rolling element contacts the surface of the airfoil-shaped body, wherein each third actuatable device is capable of changing its configuration from the first configuration to the second configuration in response to receipt of a fifth device actuation signal and changing its configuration from the second configuration to the first configuration in response to receipt of a sixth device actuation signal, the base of the chassis being movable by rolling on the rolling elements when the first actuatable device is in its first configuration and the third actuatable devices are in their second configuration, and the base of the chassis being not movable by rolling on the rolling elements when the first actuatable device is in its second configuration and the third actuatable devices are in their first configuration, wherein the computer system is further configured to perform the following operations:
after operation (b) and before operation (e), sending the sixth device actuation signal to each of the third actuatable devices; and
after operation (e) and before operation (g), sending the fifth device actuation signal to each of the third actuatable devices.

18. The automated apparatus as recited in claim 17, wherein the rolling elements comprise balls, the first actuatable device comprises a suction cup, the second actuatable device comprises an extendible/retractable foot, and each third actuatable device comprises a respective electromechanical solenoid having an extendible/retractable element connected to a respective socket that supports a respective ball.

19. The apparatus as recited in claim 1, wherein the first, second and third suction cups are arranged so that their respective centers are positioned at respective vertices of a hypothetical triangle, and the chassis further comprises a linear roller disposed in an area bounded by the hypothetical triangle.

20. The apparatus as recited in claim 1, wherein the first, second and third ball and socket bearings cups are arranged so that their respective balls are displaced from the base.

21. The apparatus as recited in claim 1, wherein the base has an opening, and the chassis further comprises a linear roller that is rotatably coupled to the base and occupies a portion of the opening.

22. The apparatus as recited in claim 1, wherein the first, second and third actuators are electromechanical solenoids.

\* \* \* \* \*